(12) United States Patent
Tomlinson, Jr. et al.

(10) Patent No.: US 7,654,148 B2
(45) Date of Patent: Feb. 2, 2010

(54) ULTRASOUND COMMUNICATION SYSTEM FOR METAL STRUCTURE AND RELATED METHODS

(75) Inventors: Harold W. Tomlinson, Jr., Scotia, NY (US); John B. Deaton, Jr., Niskayuna, NY (US); Edward Nieters, Burnt Hills, NY (US); Fergus Ross, Niskayuna, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 425 days.

(21) Appl. No.: 11/417,421

(22) Filed: May 4, 2006

(65) Prior Publication Data

US 2007/0167133 A1 Jul. 19, 2007

Related U.S. Application Data

(60) Provisional application No. 60/692,744, filed on Jun. 22, 2005.

(51) Int. Cl.
*G01N 29/04* (2006.01)
(52) U.S. Cl. .......................................................... 73/801
(58) Field of Classification Search .................. 73/801; 703/801
See application file for complete search history.

(56) References Cited

U.S. PATENT DOCUMENTS

| | | | | |
|---|---|---|---|---|
| 5,154,081 A | * | 10/1992 | Thompson et al. | ............. 73/597 |
| 5,675,554 A | * | 10/1997 | Cole et al. | ................... 367/138 |
| 7,037,270 B2 | * | 5/2006 | Seward | ........................ 600/459 |
| 7,354,400 B2 | * | 4/2008 | Asafusa et al. | .............. 600/437 |
| 2003/0189488 A1 | | 10/2003 | Forcier et al. | |
| 2004/0212504 A1 | | 10/2004 | Forcier et al. | |

\* cited by examiner

*Primary Examiner*—Max Noori
(74) *Attorney, Agent, or Firm*—Bracewell & Giuliani LLP

(57) ABSTRACT

Embodiments of the present invention beneficially provide an ultrasound communication system and methods of ultrasound communication for diagnostics and prognostics of structures. For example, ultrasound transmitters are connected to a metal or composite structure and modulated to produce Lamb waves that travel to an ultrasound receiver. The ultrasound transmitters can use frequency-hopped signals to digitally encode transducer information among different transmitters. The transmitters can be operated asynchronously. The receiver can use a channel equalizer to reduce the effects of signal multipath and a decoder to decode the transducer information from the ultrasound transmitters.

23 Claims, 29 Drawing Sheets

Transducers mounted on the A-10 Thunderbolt wing.

| Assume Aircraft Wing | | |
|---|---|---|
| Freq (Hz) | 88000 | Sound Frequency |
| V (m/s) | 5200 | Sound Velocity |
| lambda (m) | 5.91E-02 | Wavelength |
| R (m) | 17 | Separation |
| alpha-sc/ab(1/Hz-m) | 0.0001 | Combined scattering/absorption coefficient |
| alpha-m | 0.8 | Mode conversion efficiency |
| Noise BW (Hz) | 100 | Noise Bandwidth at the receiver |
| Pt (W) | 1.35E-01 | Transmitted power (10volts @ 741 ohms) |
| Gt | 0.001 | Transmit antenna efficiency, including coupling loss |
| Gr | 0.001 | Receive antenna efficiency, including coupling loss |
| EIRP (dBW) | -38.7 | Effective isotropic radiated power |
| K | 0.75 | Piezoelectric constant |
| Ls (dB) | 38.6 | Spreading Loss |
| Tabs (deg K) | 273 | Temperature |
| Teff (deg K-Hz) | 27300 | Effective temperature-bandwidth product |
| k (dB J/K) | -228.6 | Boltzman constant |
| Lm (dB) | 22.7 | Sound loss in material |
| GrK2/T (dB/k) | -76.9 | Receiver figure of merit |
| C/N (dB) | 51.7 | Carrier-to-noise ratio |
| SNR to close link (dB) | 17.0 | For BER of 10 |
| Link Margin (dB) | 34.7 | Enough for two lap joints (20dB) and 15dB of engine noise |

Estimated link margin for ultrasound propagation across a 50' wing.

*FIG. 3.*

Bandwidth and Resistance of Transducers

|  | 0.5 inch | 3/8 inch | 1 inch |
|---|---|---|---|
| Center frequency (fc) | 172.5 kHz | 212.5 kHz | 87 kHz |
| Bandwidth | 25 kHz | 27 kHz | 14 kHz |
| Impedance @ fc | 882 ohm | 1.3 K | 741 ohm |
| Angle @ fc (degrees) | 69 | 80 | 84 |
| Resistance @ fc | 144 ohm | 233 ohm | 856 ohm |
|  |  |  |  |
| Impedance (range in BW freq) | .105 - 4 K | .249 - 4.2 K | .071 - 6.4 K |
| Angle (range in BW freq) | 57-77 | 68-80 | 68-85 |
| Resistance (range in BW freq) | .038-1.4 K | .074 - 1.16 K | .024 - 2 K |

Measured Electrical Characteristics of the Ultrasound Transducers

*FIG. 4.*

Lower left corner of the plate is at (0,0)

| Transmitter (x,y) | Receiver (x,y) | Distance (inches) | Vpp (mV) |
|---|---|---|---|
| (6,12) | (12,12) | 6 | 137.6 |
| (6,12) | (18,12) | 12 | 100 |
| (6,12) | (24,12) | 18 | 92 |
| (6,12) | (30,12) | 24 | 71.2 |
| (6,12) | (36,12) | 30 | 65 |
| (6,12) | (42,12) | 36 | 49.6 |

Attenuation measurements from an aluminum plate.

*FIG. 5.*

Plot of an attenuation vs. seperation for an aluminum plate.

| Transmitter (x,y) | Receiver (x,y) | Pulse | Distance (Inches) | Time (ms) | Vpp (mV) |
|---|---|---|---|---|---|
| (23,15) | (25,15) | 1st | 2 | 8.6 | 416 |
| (23,15) | (25,15) | 2nd | 18.11 | 86 | 104 |
| (23,15) | (25,15) | 3rd | 30.07 | 141 | 32 |
|  |  |  |  |  |  |
| (23,15) | (26,15) | 1st | 3 | 13.8 | 336 |
| (23,15) | (26,15) | 2nd | 18.25 | 86 | 102 |
| (23,15) | (26,15) | 3rd | 30.15 | 142 | 50 |

Reflection coefficient measurements from an aluminum plate.

Lower left corner of the plate is at (0,0)

| Transmitter (x,y) | Receiver (x,y) | Distance (inches) | Time for 10 dB drop (ms) |
|---|---|---|---|
| (6,12) | (24,12) | 18 | 10.89 |
| (6,12) | (30,12) | 24 | 11.48 |
| (6,12) | (36,12) | 30 | 13.8 |
| (6,12) | (42,12) | 36 | 14.2 |

FIG. 11.
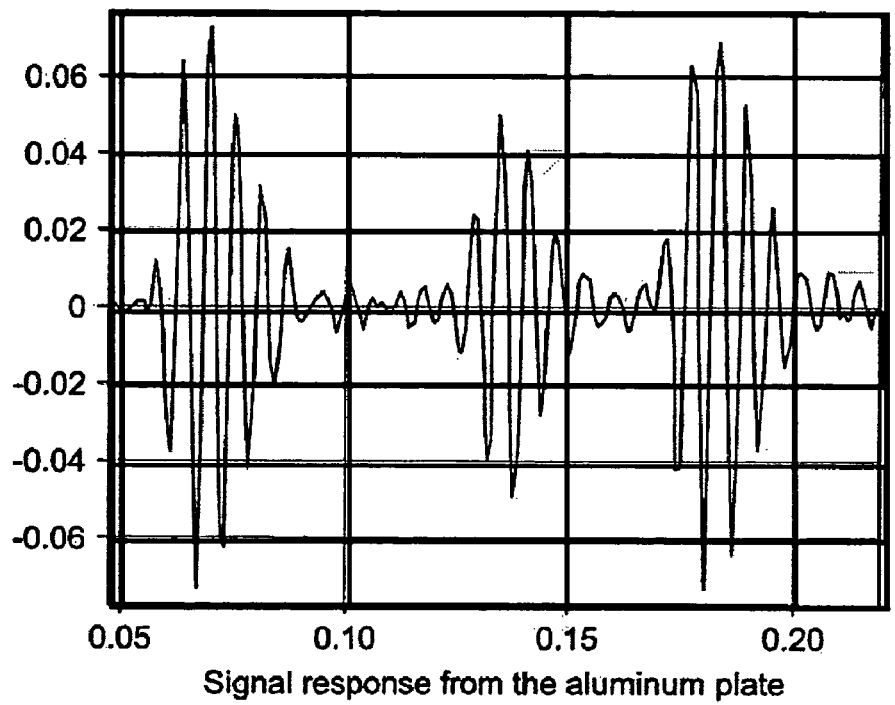
Signal response from the aluminum plate
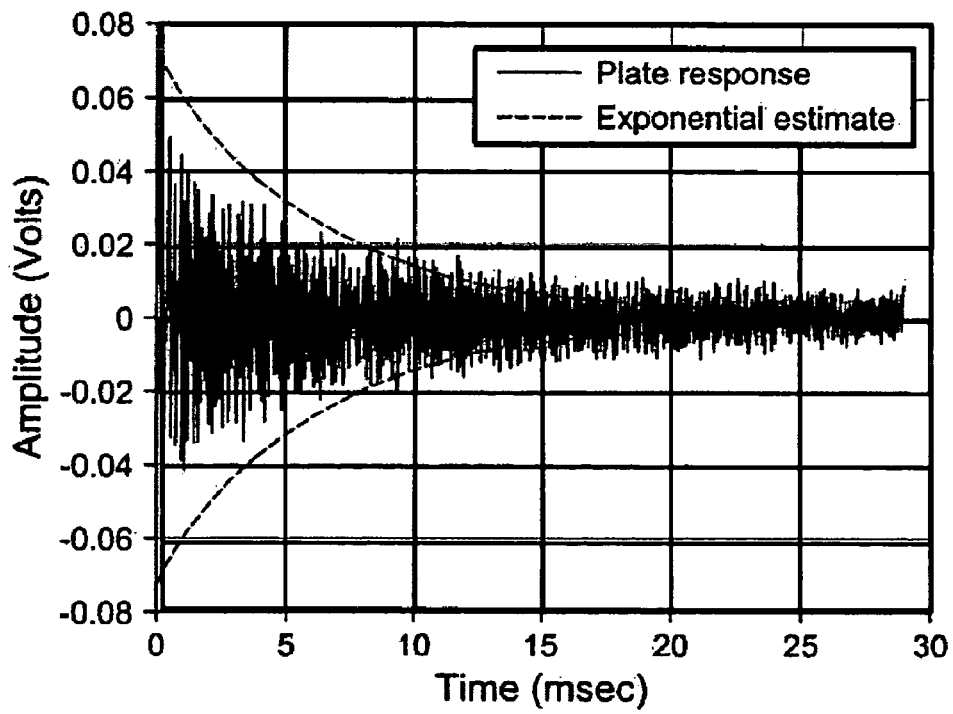
Signal response from the plate on an expanded
time scale showing multipath exponential decay.
FIG. 12.

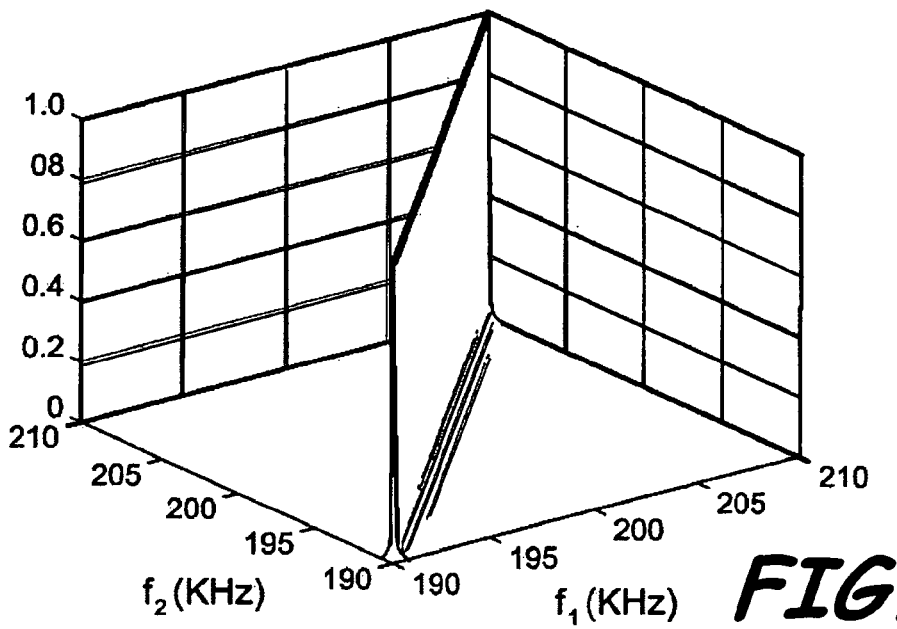
FIG. 13.
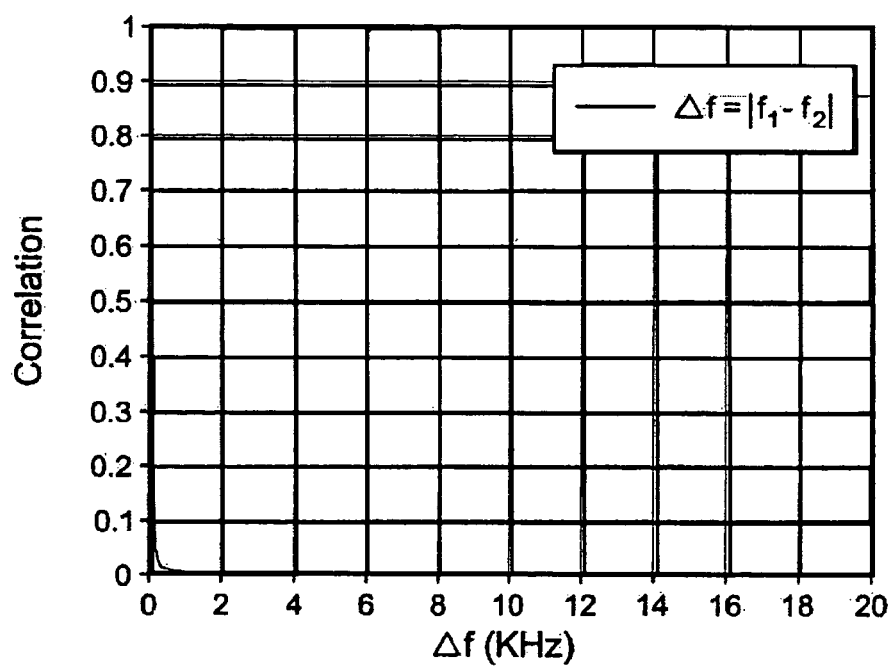
FIG. 14. Simulation Results for Correlation Detector Theoretical and simulated bit error rate vs. SNR/bit for the ultrasound demodulation approaches Diagram of the lab-based ultrasound communication system.

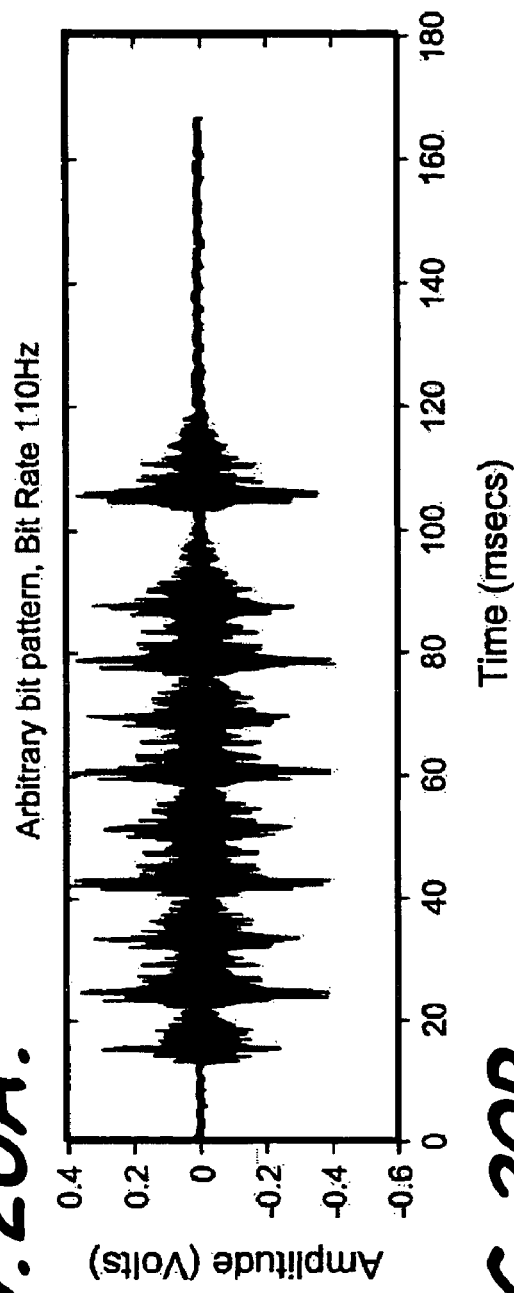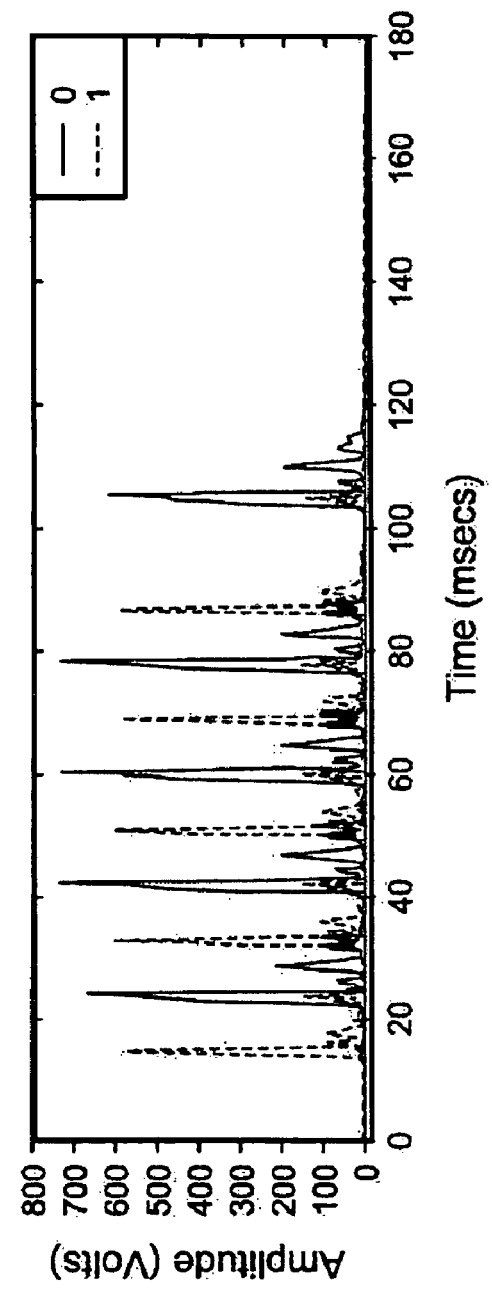
FIG. 20A.
FIG. 20B.

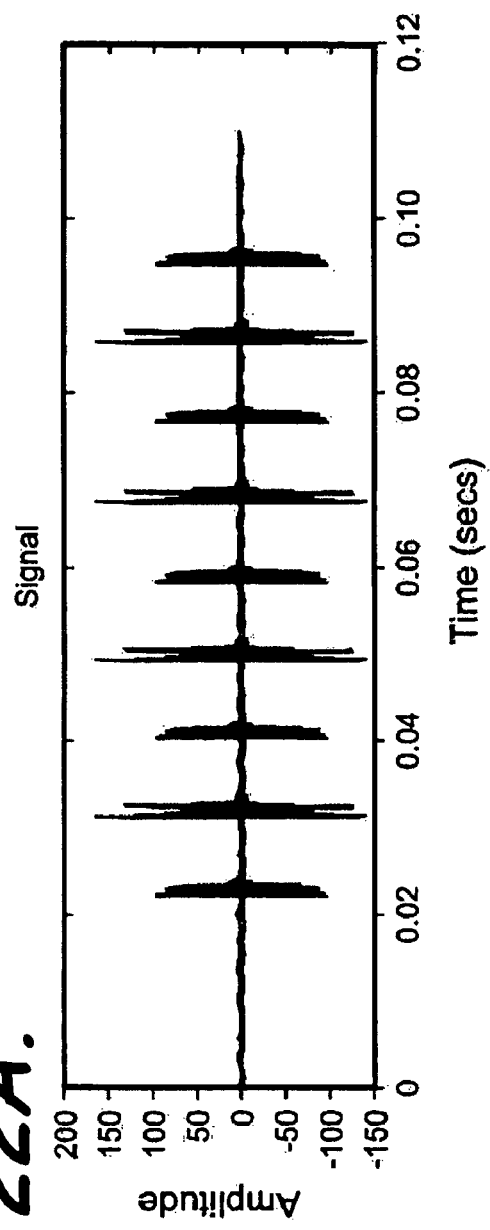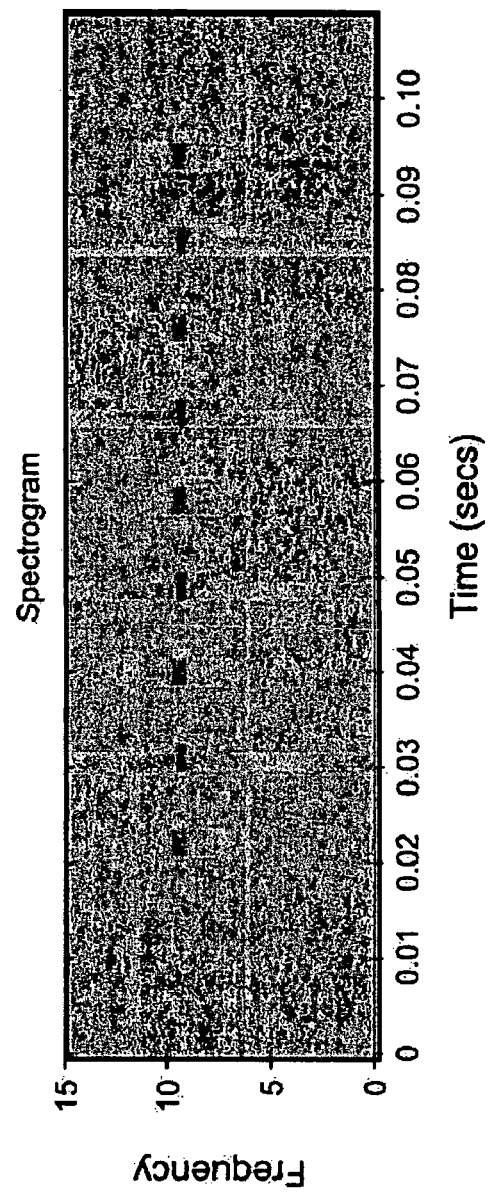
FIG. 22A.
FIG. 22B.
Received signal and corresponding spectrogram for signals received across a lap joint.

Graphite-epoxy sheet
0.125"-0.187" thick
Panel lengths to 9'

| Model Number | Normal Voltage (V) | Normal Capacity (mAh) | Max Discharge (mA) | Internal Impedance (mA) | Cycle Life (times) | Dimension (mm) | Approx Weight (g) | Price 100 - 1000 |
|---|---|---|---|---|---|---|---|---|
| Lir1620 | 3.6v | 11 mAh | 20mA | 1.2 Ohms | 500 | 16.0*2.2 | 1.2 | $1.35 |
| Lir2016 | 3.6v | 15 mAh | 24mA | 1.0 Ohms | 500 | 20.0*1.8 | 1.6 | $1.35 |
| Lir2025 | 3.6v | 25 mAh | 40mA | 0.75 Ohms | 500 | 20.0*2.7 | 2.2 | $1.35 |
| Lir2032 | 3.6v | 35 mAh | 70mA | 0.60 Ohms | 500 | 20.0*3.2 | 3.0 | $1.26 |
| Lir2430 | 3.6v | 60 mAh | 110mA | 0.60 Ohms | 500 | 24.5*3.2 | 3.7 | $1.31 |
| Lir2450 | 3.6v | 110 mAh | 200mA | 0.40 Ohms | 500 | 24.5*5.4 | 5.2 | $1.31 |
| Lir2477 | 3.6v | 160 mAh | 300mA | 0.30 Ohms | 500 | 24.5*8.4 | 7.8 | $1.46 |

Electrical characteristics of Lithium Ion coin cells.

Transducers mounted on the A-10 Thunderbolt wing.

Transducers mounted on the F-84 wing.

| Transducer Separation (feet) | Peak received signal (mv) | Propogation time (us) | Delay Spread (ms) | Comment |
|---|---|---|---|---|
| 1 | 500 | 55-58 | | |
| 4 | 40 | 232 | | |
| 8 | 15.3 | 475 | 3.8 | |
| 10 | 2.25 | 2000 | 2.8 | Across lap joint |
| 0.5 | 105 | 45 | 0.6 | Across lap joint |
| 0.5 | 280 | 38 | 1.25 | |
| 1 | 110 | 60 | | |
| 1 | 5.8-9.6 ($1^{st}/3^{rd}$ pulse) | 340 | 3.15 | Across 2 lap joints |
| -0.8 | 19.5 | 56 | 1.35 | Wing-to-fuselage |
| | | | | |

Acoustic measurements on the F-84 wing.

Acoustic measurements from the wing to the fuselage.

Propagation time for non-lap joint measurements.

Signal Attenuation vs Transducer Separation for F-84 Wing.

Shipping container measurement apparatus.

| Transmitter location | Received P-P voltage (mv) | dB attenuation relative to transmit voltage |
|---|---|---|
| Same corrugation, 12" above receiver | 120 | -38.4 |
| 1 corrugation away, 17" from receiver | 50 | -46.0 |
| 2 corrugations away | 35 | -49.1 |
| 3 corrugations away, with weld seam in between | 32 | -49.9 |
| 5 (56" from receiver) | 22 | -53.2 |
| 10 corrugations (112") | 10 | -60.0 |

Attenuation measurements for the shipping container

*FIG. 38.*

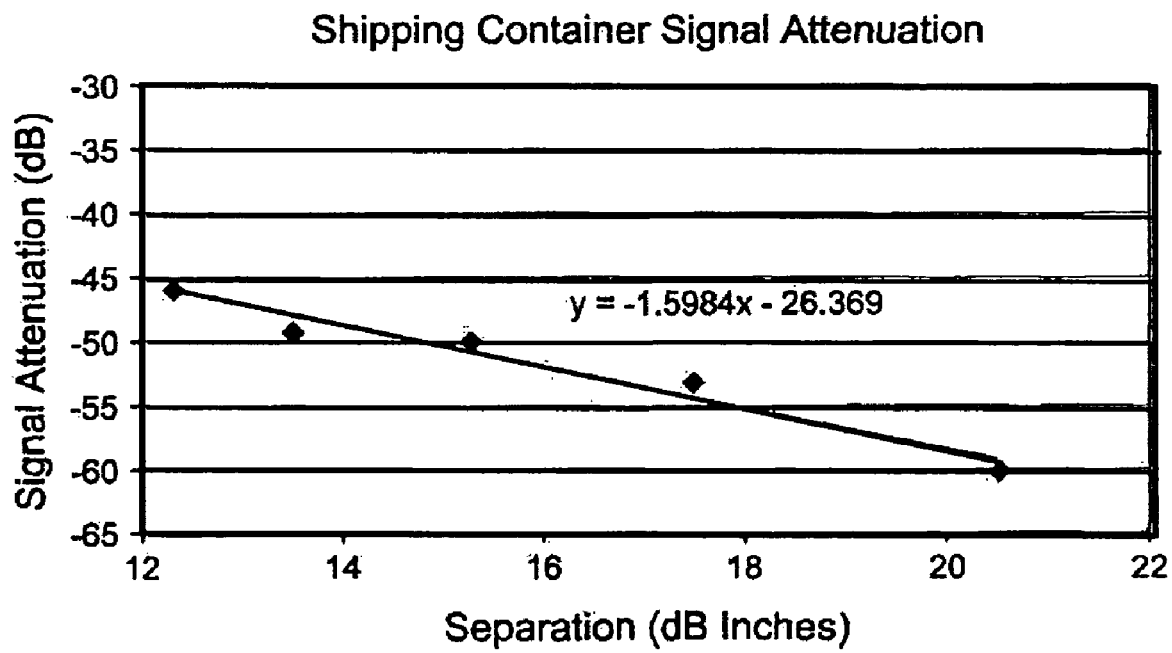

Signal attenuation vs transducer separation for the shipping container.

*FIG. 39.*

Packaging concept for a sensor node with ultrasound communication.

# US 7,654,148 B2

ULTRASOUND COMMUNICATION SYSTEM FOR METAL STRUCTURE AND RELATED METHODS

RELATED APPLICATIONS

The present application claims priority to and the benefit of U.S. Provisional Patent Application Ser. No. 60/692,744 filed on Jun. 22, 2005 titled "Ultrasound Communication System and Related Methods" and which is incorporated herein by reference in its entirety.

BACKGROUND OF THE INVENTION

1. Field of the Invention

The present invention relates to communication to and from structures and, more particularly, to systems and methods for monitoring and communication to and from structures.

2. Description of Related Art

As our military aircraft fleet ages, Applicants recognize that it will become increasing important to provide prognostic health management (PHM) of a structure such as a frame of an aircraft or other type of vehicle. For example, PHM may provide a way to predict when the aircraft structure has degraded to the point where it no longer meets safety margins due to metal fatigue. In newer aircraft made from composite materials, structural monitoring will also be required to help predict the sudden catastrophic failure of the composite, which can happen when material defects rapidly propagate in the structure. Wiring, for example, can further degrade the integrity of the structure, especially for composites, and can increase the cost of retrofitting a sensor network such as in an aircraft fleet. Today, wireless sensor network solutions are typically based on radio frequency (RF) or infrared light, but these approaches can increase the detectability of military aircraft to an enemy. In addition, RF solutions can be high power, requiring relatively large battery sources for the embedded sensors. Wireless communication via RF can produce unwanted RF signatures and interference in some applications as well. RF communication may also be impractical in some applications due to excessive multipath or RF interference.

It has been known to use ultrasound communication for in situ monitoring of an injection molding process, for example, but there is a need for in situ sensors that provide real-time measurements of material stress to provide PHM of various structures such as aircraft or other vehicles.

SUMMARY OF THE INVENTION

In view of the foregoing, embodiments of the present invention provide a system having a real-time sensor network capable of being effectively embedded in a structure such as an airframe to provide measurements to a central location. For example, data communication for an embodiment of a system having this sensor network can be wireless so that thin sensors can be easily embedded into the skin of a wing or airframe without the need to wire the sensors for power or communication. By providing embodiments of systems and methods of the present inventions which include wireless communication, the wireless communication of sensor information can reduce the installation costs of sensor networks. By utilizing the benefits of ultrasound communication, which is also wireless, problems often associated with RF communications can be eliminated.

Embodiments of the present invention, for example, provide use of ultrasound as the wireless communication mechanism for sensors embedded in a structure such as skin of a wing of aircraft. Ultrasound can be transmitted within the wing structure itself, for example, being virtually undetectable outside the aircraft. In addition to aircraft and other types of vehicles, embodiments of this system can also have application to pipeline inspection, bridge structural monitoring, and sensor communication within steel shipping containers, for example.

In embodiments of systems and methods of the present invention, for example, ultrasound transducers can be attached to metal or composite structures, including airframes, shipping containers, pipes and bridges, and used to communicate sensor information to an ultrasound receiver through the structure. Also, the ultrasound transducers coupled to the metal or composite structure can be modulated to produce Lamb waves that travel to the ultrasound receiver. The ultrasound transmitters can use frequency-hopped signals to digitally encode transducer information among different transmitters. The transmitters are operated asynchronously. The ultrasound receiver for example, can use a channel equalizer to reduce the effects of signal multipath and decode the transducer information from the ultrasound transmitters.

An embodiment of a system according to the present invention includes a structure, a plurality of ultrasound transmitters each connected to and spaced-apart along the structure to transmit modulated ultrasound communication along the structure, and an ultrasound receiver positioned remote from the plurality of ultrasound transmitters and connected to the structure to receive the modulated ultrasound communication from each of the plurality of ultrasound transmitters. The plurality of ultrasound transmitters can be networked and in communication with a modulator to modulate each of the plurality of ultrasound transmitters. The ultrasound receiver, in turn, can include a decoder to decode the modulated ultrasound communication and a channel equalizer to reduce the effects of signal multipath.

Also, a method of ultrasound communication according to an embodiment of the present invention includes mounting a plurality of ultrasound transmitters in spaced-apart relation along a structure, mounting an ultrasound receiver to the structure remote from each of the plurality of ultrasound transmitters, modulating each of the plurality of transmitters with a preselected modulation scheme, transmitting ultrasound data communication from at least one of the plurality of transmitters along the structure to the ultrasound receiver, receiving the ultrasound communication at the ultrasound receiver, and demodulating the received ultrasound communication.

Beneficially, for example, ultrasound frequencies can be selected so that they are non-dispersive based on Lamb wave propagation characteristics of the metal or composite structure. Because each of the transmitters in embodiments of the systems and methods of the present inventions are transmit only, they do not require a receiver with which to become synchronized. Therefore, the transmitters can be significantly simplified as compared to other known transmitters in this field. An array of transducers can also be used at the receiver. This offers the possibility of increased communication range and/or reduced interference, and/or reduced multipath. In both cases, transducer arrays can allow more possibilities for locating sensors and network layout. In some instances, outbound messages may be destined for a receiver that is beyond reach. In this case, the use of intermediate nodes to relay data can be used. One example is a dummy node which simply amplifies received signals. A second example is demodulation to an alternate frequency. A third example is decoding and retransmission.

BRIEF DESCRIPTION OF THE DRAWINGS

Some of the objects and advantages of the present invention having been stated, others will become apparent as the description proceeds when taken in conjunction with the accompanying drawings, in which:

FIG. 3 is a table illustrating an estimated link margin for ultrasound propagation across a 50 foot wing of an aircraft according to an embodiment of the present invention;

FIG. 4 is a table illustrating measured electrical characteristics of ultrasound transducers of an embodiment of a system according to the present invention;

FIG. 5 is a table illustrating attenuation measurements from an aluminum plate according to an embodiment of a system and method of the present invention;

FIG. 11 is a graph of signal response from an aluminum plate according to an embodiment of a system of the present invention;

FIG. 12 is a graph of signal response from an aluminum plate on an expanded time scale showing multipath exponential decay according to an embodiment of a system of the present invention;

FIG. 13 is a graph of correlation versus frequency according to embodiments of systems and methods of the present invention;

FIG. 14 is a graph of simulation results for a correlation detector according to embodiments of systems and methods of the present invention;

FIG. 20A-20B are graphs illustrating received signal and demodulation output for a transmitted bit pattern according to an embodiment of a system of the present invention;

FIG. 22A-22B are graphs of a received signal and corresponding spectrogram for signals received across a lap joint of a metal structure according to an embodiment of a system of the present invention;

FIG. 38 is a table illustrating attenuation measurements for a shipping container structure according to an embodiment of a system of the present invention;

FIG. 39 is a graph of signal attenuation versus transducer separation for a shipping container according to an embodiment of a system of the present invention.

DETAILED DESCRIPTION

The present invention now will be described more fully hereinafter with reference to the accompanying drawings in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As illustrated in FIGS. 1-40, and as described herein, embodiments of systems and methods of the present invention can be applicable to an airplane structure or a shipping container, for example. As understood by those skilled in the art, however, the present invention is also applicable to piping, bridges, and other structures as well. Ultrasound communication in an airframe for example, requires the efficient propagation of ultrasound energy in metal structure of the airframe. Because a focus of some embodiments of the present invention is on airplane structures, such as wings, a structure to exploit within an airframe can be the aluminum wing skin, for example. As understood by those skilled in the art, ultrasound propagation in thin metal plates generally takes the form of a guided wave where the wave propagation is guided between the two parallel surfaces of the plate. For a plate sufficiently thin to allow penetration to the opposite surface, e.g., a plate having a thickness of the order of a wavelength, the waves are referred to as Lamb waves named for Horace Lamb, in honor of his fundamental contributions to this subject, which can be propagated in a number of modes, either symmetrical or antisymmetrical.

Figure 1:
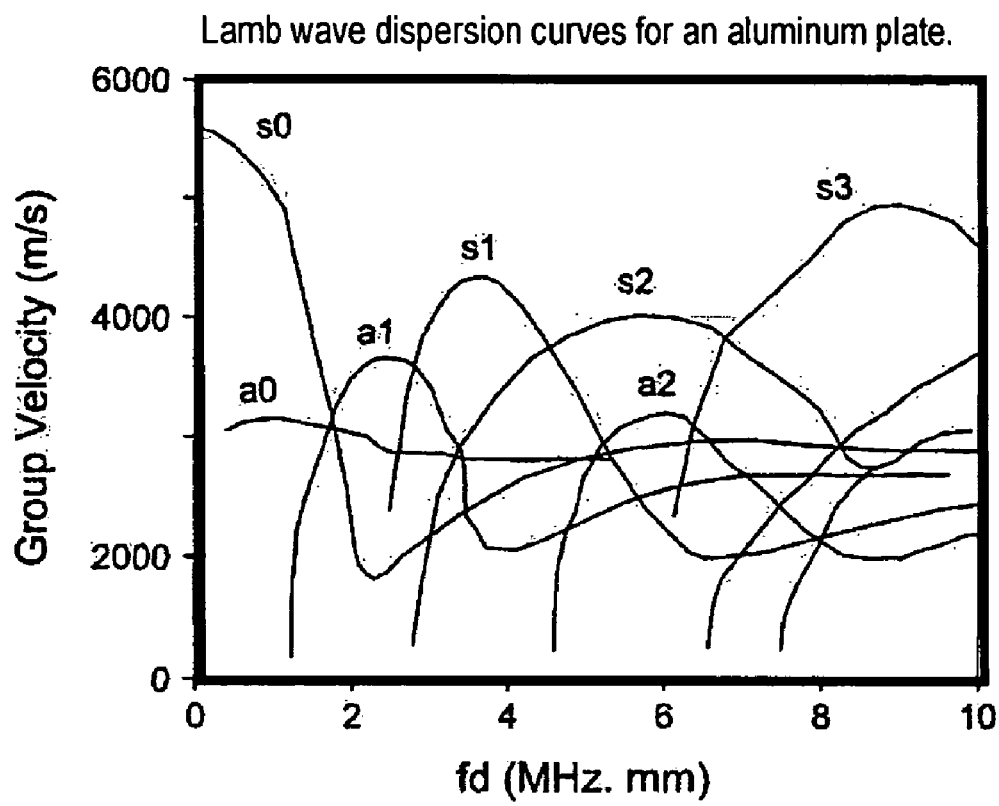
FIG. 1 is a graph of Lamb wave dispersion curves for an aluminum plate illustrating frequency versus velocity according to an embodiment of a system and method of the present invention.

FIG. 1 shows a graph of the Lamb wave velocity as a function of the produce of frequency and plate thickness. The modes s0, s1, s2, and s3 are the symmetric propagation modes, and the modes a0, a1, and a2 are the antisymmetric modes. Note that the Lamb waves are highly dispersive, which can have implications on the type of modulation used in an ultrasound communication system.

Embodiments of a communication system 60 according to the present invention, for example, can transmit a voltage reading (0-10V) at 8-bits through 50 feet of aluminum plate, with (0.060 inches to 1.0 inch) thickness, and having acceptable signal-to-raise ratio (SNR) for low-data rate communication (1 reading/minute). Communication preferably is one way and can accommodate at least 10 sensors, for example.

Figure 2:
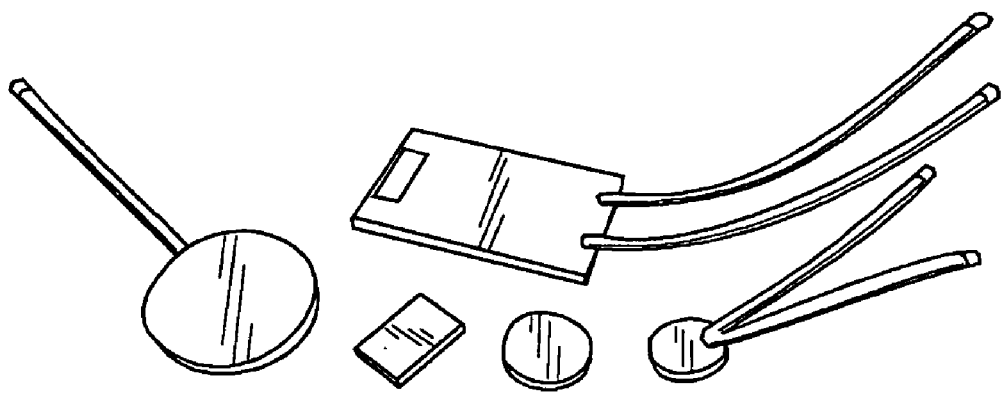
FIG. 2 is a perspective view of various piezoelectric transducers of an embodiment of a system according to the present invention.

A number of different ultrasound transducers technologies, such as the transducers 50 shown in FIG. 2, are available for generating ultrasound energy. As understood by those skilled in the art, piezoelectric ceramic disks, Macro Fiber Composite (MFC) piezo patches, and Capacitive Micromachined Ultrasound Transducers (CMUTs) are some of the available technologies (see, e.g., FIG. 2). Piezoelectric disks are relatively thin (1-2 mm), relatively inexpensive, and efficient, but can have limited bandwidth because their resonant frequency is a function of the disk diameter. CMUTs are small and wideband, but can be relatively inefficient transducers. MFC patches may be a useful technology as their efficiency is relatively high, they are wide bandwidth, and very thin. Embodiments of systems and methods of the present invention, however, can be applicable to these and other developing transducer technology. So, for example, readily available piezoelectric disks such as from APC International (see, e.g., http://www.americanpiezo.com/) can be used.

When laying out or planning an installation of embodiments of an ultrasound communication system, to determine the feasibility of using ultrasound for sensor communication, a number of questions may be used for such analysis. For example, 1) Is there enough signal-to-noise ratio (SNR) to allow one-way transmission of sensor data over 50 feet? One advantage of embodiments of a system of the present invention is that the sensor transmission can be one-way to a single receiver. This allows a complex receiver to be used in order to reduce the complexity of the transmitter, but only if transmissions can reach from the furthest sensor node such as on a wing to a remote receiver such as in the fuselage.

2) What is the magnitude of the multipath reflections that can be expected during ultrasound communication? Are there approaches to mitigate the effect of the multipath and improve signal reception? As understood by those skilled in the art, there are a number of approaches to communicating in the presence of strong multipath used in RF communication that can also be applied to ultrasound communication.

3) How much engine noise is present in the ultrasound communication band? To answer this question, arrangements to make acoustic measurements at test facilities can be made.

4) What modulation scheme should be used?

5) What is the channel capacity?

6) How much power would be required to transmit an ultrasound message?

The approach used to examine these analytical research questions, for example, can be to understand the basic parameters that determine the SNR of ultrasound communication in a metal plate, and measure the parameters in the lab and on an aircraft wing structure. A modulation approach can then be designed and tested in an experimental setup to demonstrate feasibility of ultrasound communication through such a wing structure. Development of an acoustic model also can be used to help answer some of the communication questions, but the complexity of the model that would be required to adequately simulate the wing structure can make such an analysis more difficult.

The following link budget is an example of what can be developed to estimate the required transmit power needed to communicate ultrasound over a given distance in a metal plate according to embodiments of systems and methods of the present invention. The link budget takes into account multipath reflections, but is meant to give an idea of the carrier-to-noise ratio (C/No) available under best-case propagation conditions. The expressions can allow one to determine the effect of various operating parameters on C/No and determine whether self-powering of an ultrasound transmitter is at all feasible.

For example, the following assumptions can be made:

A piezoelectric ultrasound transmitter 52, 52' and a receiver 72, 27' are placed on a metal plate 55 of infinite size. Separation between the transmitter 52, 52' and receiver 72, 72' is R. Lamb wave propagation in the material is assumed.

The power (C) received by the receive transducer of the receiver is given by:

$$C = P_t A G_t L_r$$

Where:
P$_t$ is the transmitted power
A is the attenuation from spreading loss, sound absorption in the material (material and frequency dependent), and efficiency of the propagating mode.
G$_t$ is a measure of the efficiency of the transmitter
L$_r$ is the effective length of the receive transducer The attenuation, A, can be broken down into spreading loss and material loss factors. The spreading loss is confined to a two-dimensional (2D) plane, which is different from the typical three-dimensional (3D) loss in RF communication systems. In the 2D case, the loss factor will be:

$$1/(2\pi R)$$

This is considerably better than the 1/R$^2$ spreading loss of typical wireless RF communications. Attenuation from the material is composed of a frequency dependent factor from sound absorption in the material, and a scattering component, and the mode efficiency. The sound absorption is generally a function of frequency, and can be expressed as:

$$\alpha_{ab} RV/\lambda$$

Where:
$\alpha_{ab}$=absorption coefficient (dB/m-hz)
V=velocity of sound in the material The scattering coefficient, $\alpha_{sc}$, is shown to be a function of the frequency to the fourth power, but because material scattering is generally small in the materials of interest, the scattering coefficient can be represented as being frequency independent. The mode efficiency can be represented as $\alpha_m$.

The link budget equation can now be written as:

$$C = P_t G_t G_r \lambda \alpha_m / (2\pi R^2 \alpha_{sc} \alpha_{ab} V)$$

where G$_r$ is measure receive antenna gain. In the far-field, the receive transducer efficiency will be maximum when its width is approximately $\lambda/2$. The matching of the transducer width to the wavelength is accounted for in the Gr factor.

Assuming the receive antenna is thermal noise limited, the Johnson noise in the receiver is:

$$V^2 = 4kTBr$$

Where:
k=Boltzman constant
T=temperature
B=noise bandwidth
r=equivalent noise resistance.

For a piezoelectric transducer, the power of the sound wave in the material is:

$$V^2/(r\kappa^2)$$

Where:
$\kappa$=piezoelectric coupling constant
V=voltage generated by the transducer.
The acoustic power due to the noise is then:

$$4kTB/\kappa^2$$

The Carrier-to-noise ratio is then:

$$C/N = P_t G_t G_r \lambda \kappa^2 \alpha_m / (8\pi R^2 \alpha_{sc} \alpha_{ab} V k TB)$$

Taking the log of both sides of this equation and eliminating the bandwidth dependency can form a link budget equation that resembles a typical RF link equation.

$$C/N_o = EIRP - L_s + G_r \kappa^2/T - k - L_m$$

Where:
C/N$_o$ is measured in dBHz
EIRP=Pt Gt in dBW
Ls=$8\pi R/\lambda$ in dB
Gr$\kappa$2/T in dB/K
Lm=$\alpha$sc $\alpha$ab V R/($\alpha$m $\lambda$) in dB
k=−228.6 dB J/K Note that there is a linear relationship to the acoustic wavelength and an inverse square relationship to transducer separation. Therefore, lower acoustic frequencies are preferred as long as they propagate well in the material (high $\alpha_m$). Also note that in a high multipath environment, the received power can actually be higher than that represented by this link budget if the energy from multiple reflections can be combined properly.

One way to increase C/N$_o$ is to increase the G$_r\kappa^2$/T term. This can be accomplished by using a large receive transducer to capture more transmitted energy from the sensors. In the aircraft sensor application, for example, only one receiver can be located in the fuselage. So, for example, it can be made as large as practical. There is also the possibility of using a phased array receiver as understood by those skilled in the art.

The amount of noise in the link budget will be a function of the environmental noise generated from the aircraft engines, and the electronic noise from the transducer. Because the electronic noise can be made very low, aircraft engine noise can be used to determine the noise level in the link budget equation. Generally, aircraft engine rotating components will have fundamental frequencies below 50 kHz, so the noise will be a function of harmonics of the rotating components that appear in the ultrasonic frequency range of the receiver (50 kHz-300 kHz). It may be difficult to find any measurements of ultrasonic noise in aircraft engines, so this noise can be measured, such as in a test facility, to determine the final C/No that can be obtained for an ultrasonic communication system.

To estimate the C/No ratio for an aircraft wing, the absorption/scattering coefficient and transducer coupling efficiency can be estimated from the aircraft wing measurements and placed into a link budget equation as described herein and illustrated (see also FIG. 3). For example, in an example of an embodiment of a system 60, the noise can be assumed to be from the transducer 50 only (no aircraft engine noise was assumed in this example). The transducer separation was 17 meters (50 feet). From this estimate, a C/No of 52 dB was obtained. From the bit error rate versus SNR curve for the modulation scheme of this example (see FIG. 15), 17 dB SNR is needed to obtain a bit error rate of 10$^{-3}$. Therefore, a link margin of 52 dB-17 dB=35 dB is obtained. Assuming 10 dB attenuation for a lap joint 85 (see FIGS. 21 and 23), there is enough C/No to close the link with two lap joints in the path, and still have a 15 dB margin for aircraft engine noise.

In this example, acoustic measurements were made on an aluminum plate 55 measuring 4 ft.×2 ft. and 0.061 inches thick. The measurement provided an estimate of the attenuation characteristics of Lamb wave propagation and the amount of multipath that can be expected in a small aluminum plate. The transmitter 52 included an Agilent 33200A arbitrary waveform generator 56 directly driving piezoelectric disks 50 from APC International (p/n D-1.000-0.100-850). The receiver 72 included another piezoelectric disk 70 directly attached to a digital oscilloscope 76. The transmitter and receiver disks 50, 70 were coupled to the aluminum plate 55 using shearwave couplant (Sonotech Shear Gel). Prior to the measurements, three disks operating at different resonant frequencies were characterized. The electrical properties are summarized in the table of FIG. 4 illustrating bandwidth and resistance of transducers. The aluminum plate measurements were made using the 0.5 inch disks. The sound velocity was measured to be approximately 5300 m/s, corresponding to the s0 Lamb wave propagation mode in an aluminum plate.

Consistent measurements of attenuation and reflection coefficients of the Lamb waves in the aluminum plate 55 were difficult to obtain. This may have been from variations in coupling efficiency of the disks 50, 70 to the aluminum plate 55 when the disks 50, 70 were moved to new locations on the plate 55, or due to wave mode conversions when waves reflected off the edges of the plate. The following measurements were taken using a 0.5-inch wafer. A burst of 1 square wave at 180 kHz with a burst period of 50 ms with peak-to peak of 20 volts (i.e., 2.77 ms width pulse every 50 ms) was used to excite the transducer 50. The peak-to-peak voltage of the first arriving pulse at the receiver 72 was recorded for various transmitter/receiver separations. The results are summarized in the table of FIG. 5.

Figures 6, 7:
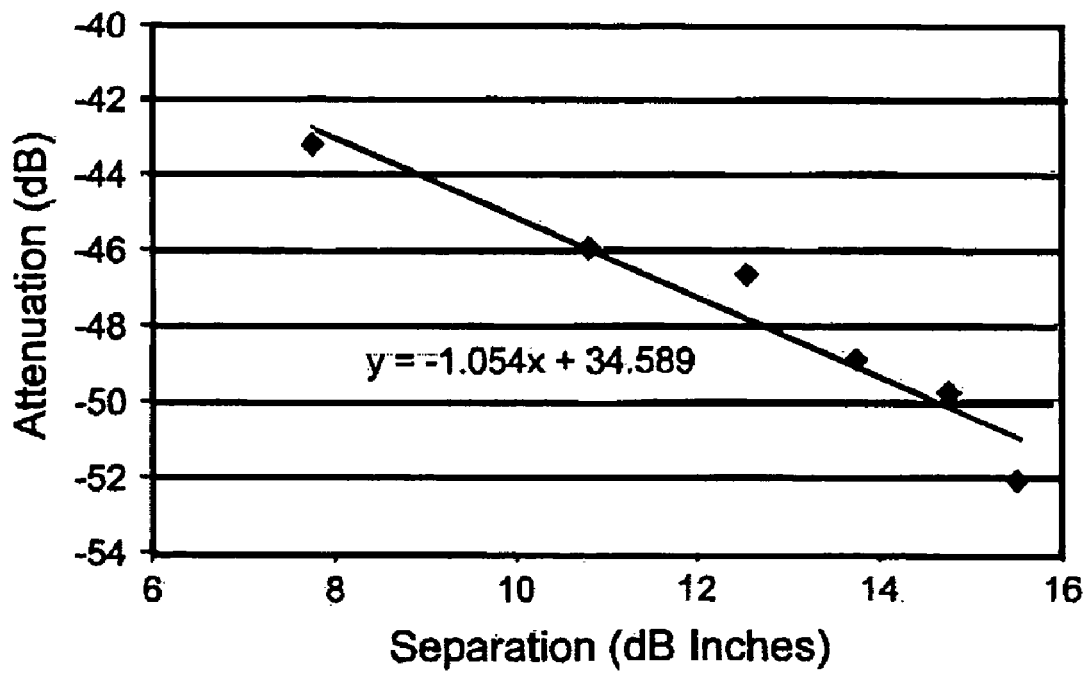
FIG. 6 is a graph of attenuation versus separation for an aluminum plate according to an embodiment of a system and method of the present invention.
FIG. 7 is a table illustrating reflection coefficient measurements from an aluminum plate according to an embodiment of a system and method of the present invention.

The attenuation measurements are plotted in FIG. 6 in a db format (log-log). In such a plot, the slope of the line indicates the exponent of the distance attenuation factor. According to the link budget, the $L_s$ spreading loss factor should follow a 1/R relationship, or an exponent of 1.0. The slope of the best-fit line in the attenuation plot is 1.05, indicating that virtually all of the attenuation loss is from spreading loss (1/R), and very little loss is from sound absorption and scattering ($L_m$). This indicates and confirms that the ultrasound signal can propagate in an aluminum plate 55 with very little attenuation in the 200 kHz frequency range.

Reflection coefficient measurements were made by measuring the peak-to-peak voltage of the ultrasound pulse that was received after reflecting off an edge in the plate 55. The velocity of sound, transmitter/receiver location and plate geometry were used to compute the propagation time of the received pulses that were expected in the measurement. The results are shown in the table of FIG. 7. The reflection measurements are plotted below in a db format (log-log) similar to the attenuation measurements. The line of slope 1.0 indicates what the attenuation of the transmitted pulse would be with just the 1/R spreading loss. Losses in excess of the spreading loss will be mostly from the pulse reflection off the sides of the plate. For the geometry tested, the first pulse was a direct pulse (no reflections), but both the second and third received pulse experienced one reflection.

Figures 8, 9:
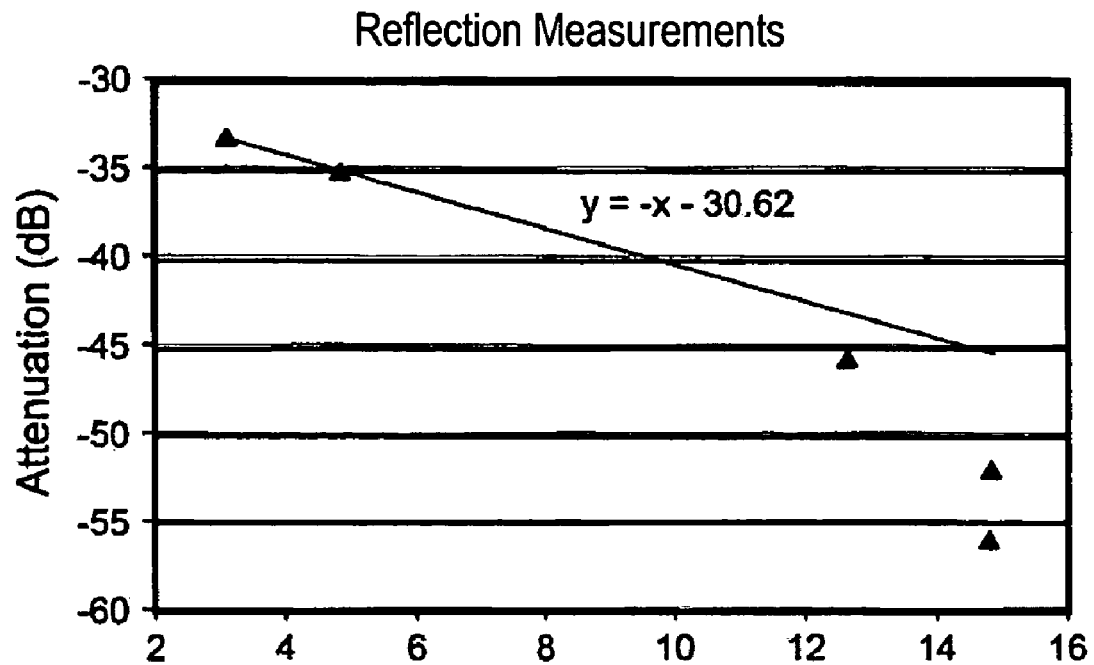
FIG. 8 is a graph of attenuation versus separation for the reflection measurement data of FIG. 7 according to an embodiment of a system and method of the present invention.
FIG. 9 is a table illustrating distance and time for 10B drop of transmitter to receiver communication in a lower left corner of an aluminum plate according to an embodiment of a system according to the present invention.

From the plot in FIG. 8, the second pulse experienced a 2 dB reflection loss, while the third pulse experienced a 6-10 dB loss. These measurements indicate that most of the ultrasound pulse energy is maintained after a reflection off the sides of the plate 55, 55', 55", which is why the multipath energy at the receiver is high for ultrasound systems. It also means that pulse transmission over large distances can occur even when a direct path between the transmitter 52 and receiver 72 is blocked.

Figure 10A:
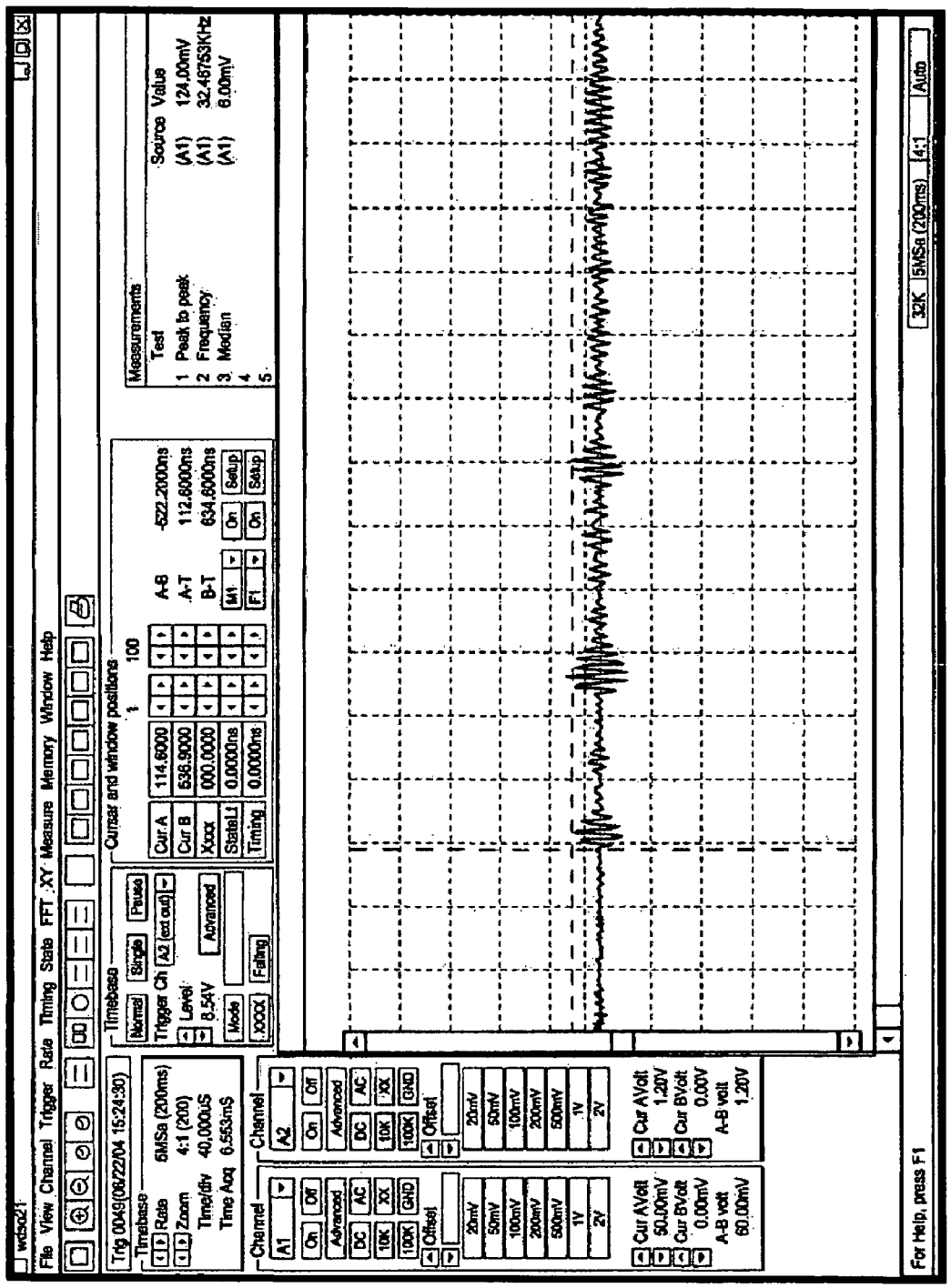
FIG. 10A is a graphical user interface of a display illustrating a graph of received ultrasound signal showing multiple reflection according to an embodiment of the present invention.
Figure 10B:
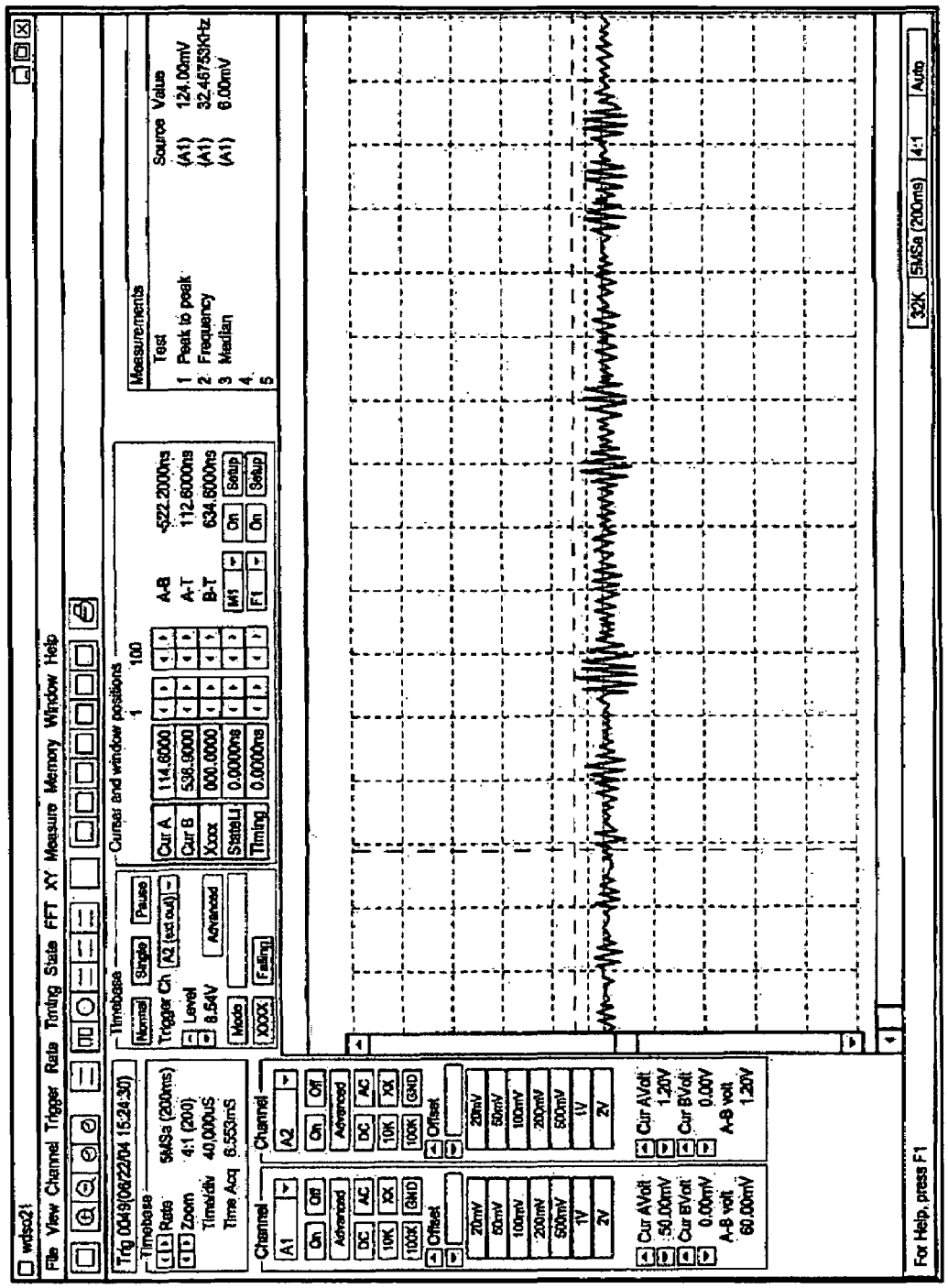
FIG. 10B is a graphical user interface of a display illustrating a graph of burst period at 10 milliseconds (ms) 1 square wave (180 kHz) according to an embodiment of a system of the present invention.
Figure 15:
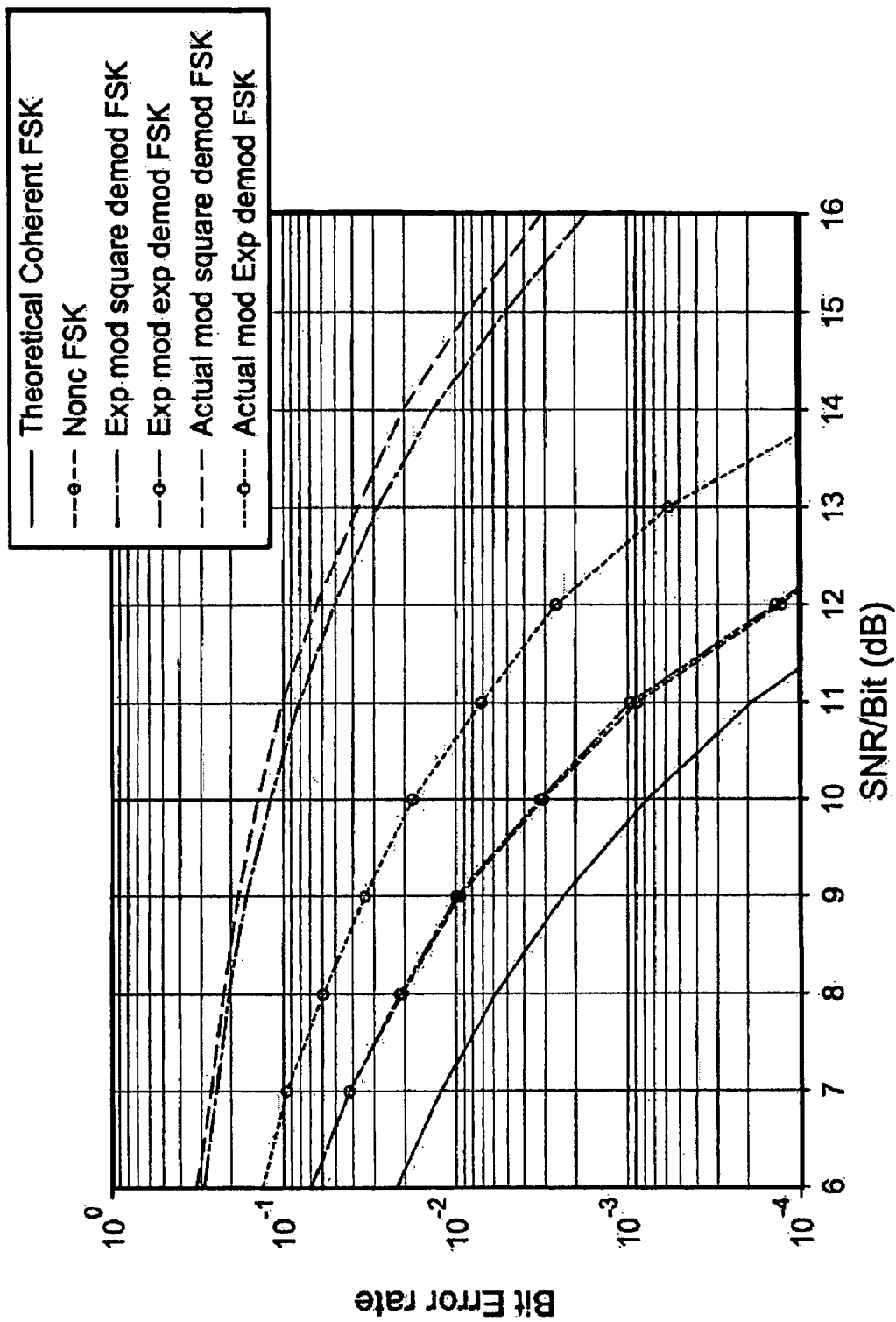
FIG. 15 is a graph of theoretical and simulated bit error rate versus signal to noise ratio (SNR) versus SNR/bit for ultrasound demodulation according to embodiments of systems and methods of the present invention.

Delay spread refers to the time over which most of the energy is received from a transmitted pulse. It depends on the geometry of the plate the position of the transmitter 52 and receiver 72, and the attenuation characteristics of the transmitted pulse in the medium. Measurements were taken at different transmitter/receiver separations using a 0.5 inch wafer and a burst of 1 square wave at 180 kHz, with a burst period of 50 ms, with peak-to peak of 20 volts (i.e., 2.77 microsecond width pulse every 50 ms). The results are shown in the table of FIG. 9. From these measurements, it appears that most of the multipath energy has dissipated after 10-15 ms, although some measurable energy persists as long as 30-40 ms. A view from one of the measurements is illustrated in FIGS. 10A-10B. Burst period is at 50 ms, 1 square wave (180 kHz), Vpp 20 volts, and green vertical line time of first wave arrival for transmitter (12, 12) and receiver (36, 12) is shown in FIG. 10B.

After the basic parameters associated with ultrasound pulse propagation in an aluminum plate were measured in this example, an apparatus or system 60 was set up to try and communicate using modulated ultrasound in the plate. First, the modulation scheme used for the data communication is described herein, and then the experimental apparatus used to test the approach is described herein.

The modulation scheme for communicating over the surface of the 4 ft.×2 ft.×0.061-inch aluminum plate was frequency shift keying (FSK) as understood by those skilled in the art. A binary non-coherent FSK receiver structure was used for demodulation. The signal is demodulated using all the energy that is received in between bit transmissions, in order to use as much of the multipath energy as possible.

Examples of plate response to a pulse 2.78 µs long (20 Vpp) is plotted in FIGS. 11-12. The signal oscillates at a frequency of 180 kHz. As all the reflections are received, the amplitude of the reflected signals decays exponentially. The amplitude plate response can be approximated by a first order exponential function ($Ae_{\alpha t}$) with exponent α=−139. Note that a 0.5-inch wafer was used with the transmitter and receiver 12 inches apart in the middle of the plate.

As understood by those skilled in the art, Matlab simulation was used to verify the operation and performance of demodulation. For the simulation, the transmitted signal was a sinusoid (square), an exponentially decaying sinusoid (Exp), or a sinusoid multiplied by the signal envelope of the actual plate response (Actual). The received signal was correlated (demodulated) at the receiver using either a sinusoid or an exponentially decaying sinusoid.

Therefore, the sinusoid signal used for modulation/demodulation was:

| Modulation | Demodulation |
|---|---|
| square | square |
| Exp | square |
| Exp | Exp |
| Actual | square |
| Actual | Exp |

For orthogonal non-coherent FSK, the frequencies should be separated by m/T (i.e., $\Delta f(|f_1-f_2|)$, where m is a positive integer and T is the bit period. This orthogonality rule is only true for square-square mod-demod scheme. This does not apply to exponentially decaying sinusoids (Exp-Exp mod-demod). Numerical simulation, however, suggests that the correlation using exponentially decaying sinusoids (Exp-Exp) decreases rapidly as Δf increases (see FIGS. 13-14). It should be noted that in FIGS. 13-14, the correlation i.e., not exactly equal to zero for large Δf.

Simulation parameters:
Fs=5 MHz. . . . Sampling frequency
$f_1$=190-210 kHz;
$f_2$=190-210 kHz
Bit period (T)=50 msec (20 Hz);
α=−139

Theoretically, the bit error probability for binary orthogonal coherent FSK is where z is the SNR and Q is the Q function. The probability of error versus SNR is plotted in FIG. 15 together with the signaling schemes discussed above. Note that there is a big gain (~4 dB) using Actual-Exp versus Actual-square mod-demod scheme. Simulation parameters:

Fs=1 MHz;
f₁=199 kHz;
f2=200 kHz;
Bit period=50 msec (20 Hz);
α=−139

Figure 16:
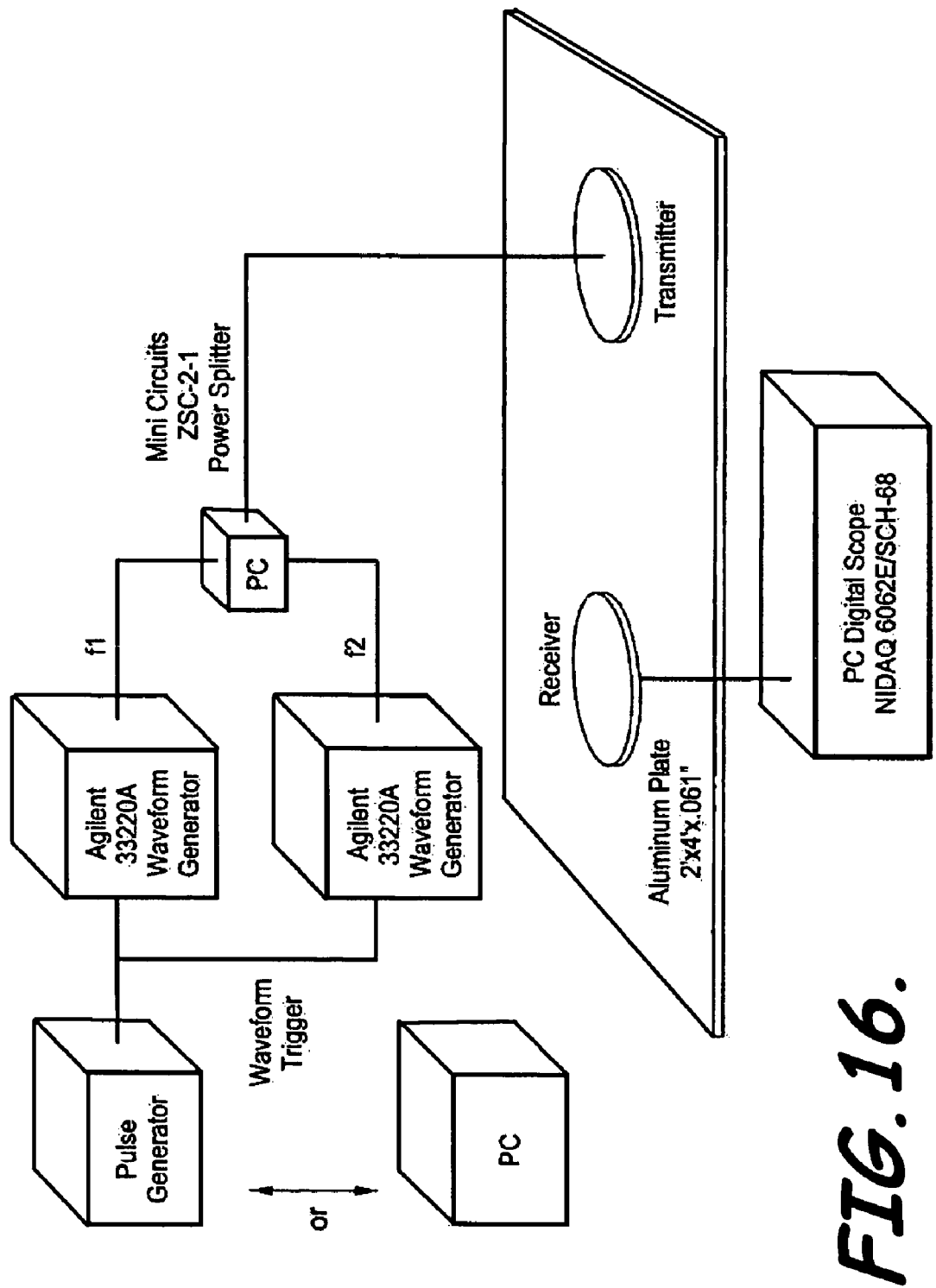
FIG. 16 is a schematic diagram of a an embodiment of a system of the present invention.

The modulation and detection scheme also was tested on the aluminum plate 55 in this example. The transmitter apparatus consisted of two arbitrary waveform generators 56, a pulse generator 57 and a signal adder 54 to generate the input signal. One waveform generator was used to generate a burst of N cycles at frequency 1 (f1), while the other was used to generate N cycles at frequency 2 (f2). The pulse generator 57 (or a personal computer 58) was used to trigger the frequency burst in the waveform generators, with a negative transition triggering f1, and the positive transition triggering f2. The outputs of the generators were combined using the signal adder 54, then fed to the piezoelectric disk 50. The receiver 72 was implemented using a data acquisition system that digitized and stored the received ultrasound waveform. As understood by those skilled in the art, a Matlab program was used to demodulate the waveform into the transmitted bit pattern (FIG. 16).

Figure 17A:
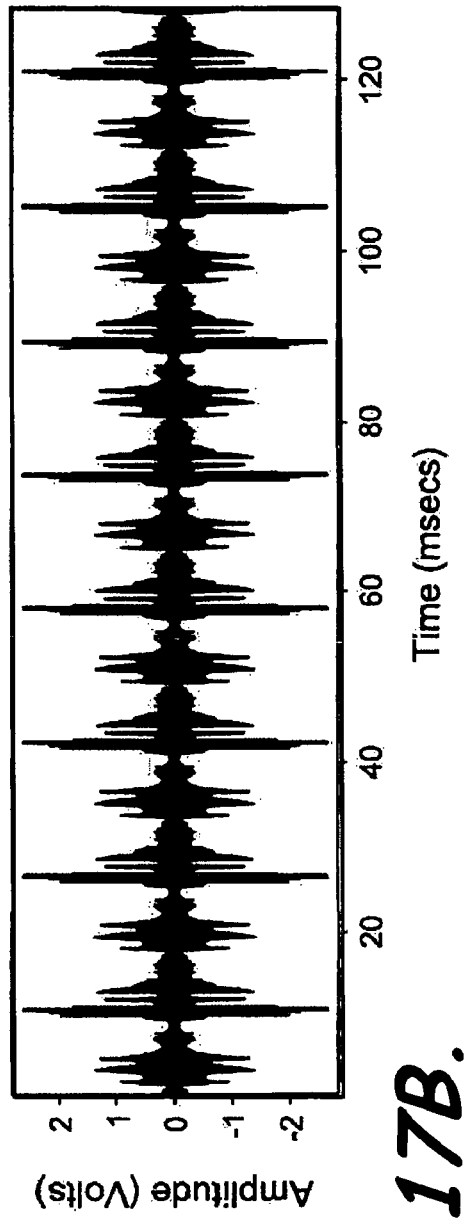
FIG. 17A-17B are graphs illustrating received signal and demodulation output for a selected bit pattern according to an embodiment of a system of the present invention.
Figure 17B:
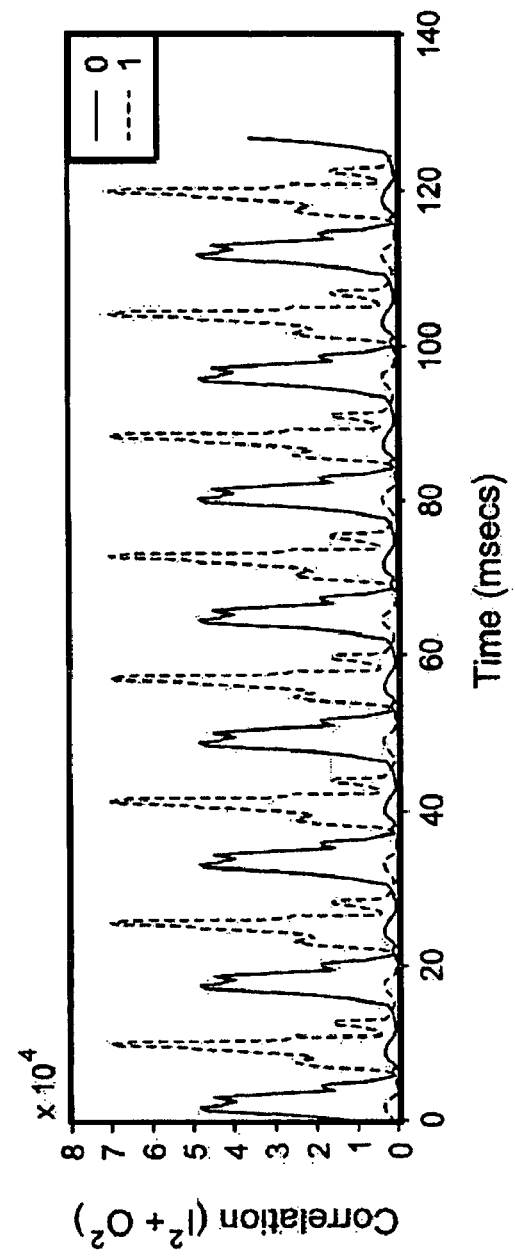
Figure 18A:
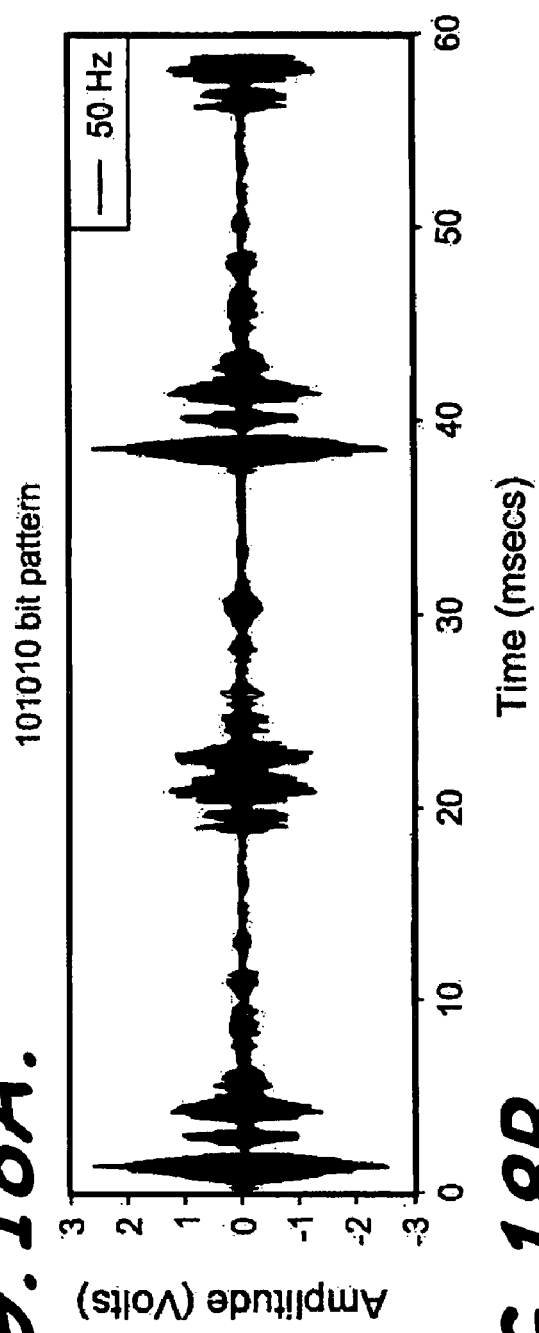
FIG. 18A-18B are graphs of received signal at 50 and 100 bits per second (bps) respectively according to an embodiment of a system of the present invention.
Figure 18B:
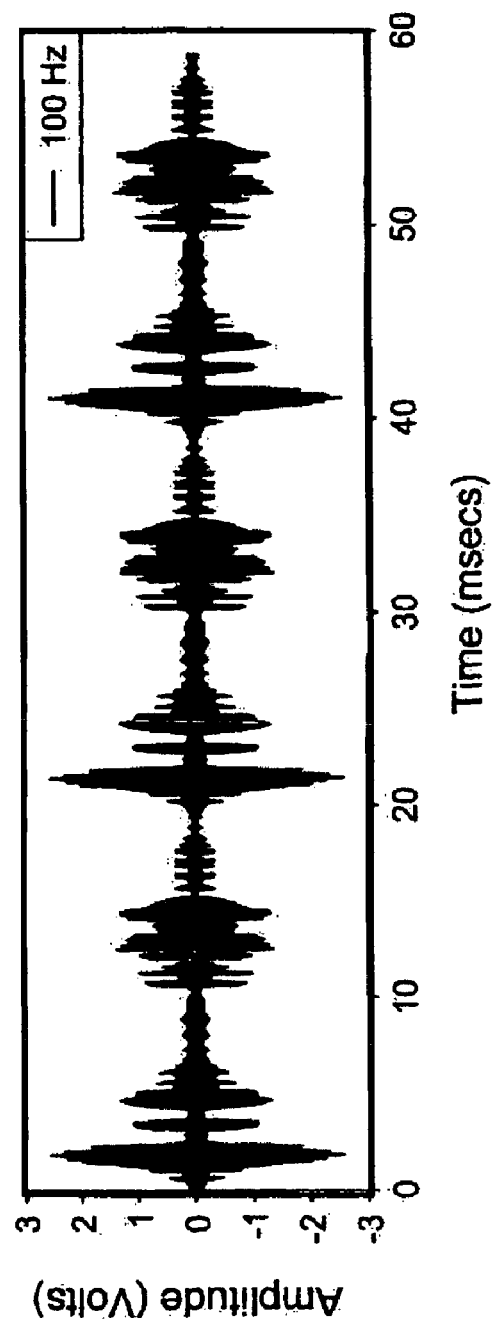

It was determined that the signal amplitude from the function generator should be less than 2 Vpp to prevent harmonics generated by the transducer (used 1 Vpp and amplified+40 dB the received signal). A 1-inch wafer was used for transmitter/receiver pair. A PC oscilloscope 76 was used to digitize the signal from the receive disk 70. On a first set of tests, a 101010-bit pattern was sent using the pulse generator with bit rates 20, 50, 100 and even 112 bps. A burst of 100 cycles of f1 (0) or f2 (1) was used for modulation. Successful demodulation was achieved on all bit rates. The correlation (I^2+Q^2) plot in FIGS. 17A-17B shows that successful demodulation can be achieved if the correlation is sampled correctly. The plot of FIG. 17A shows the raw received signal. In the plot of FIG. 17B, the respective curves are the correlation values for binary 0 and 1. At higher bit rates (greater than 50 bps), inter-symbol interference (ISI) became a problem due to the large delay spread in the aluminum plate. FIGS. 18A-18B illustrate that ISI is apparent when increasing bit rate from 50 to 100 bps.

Figure 19:
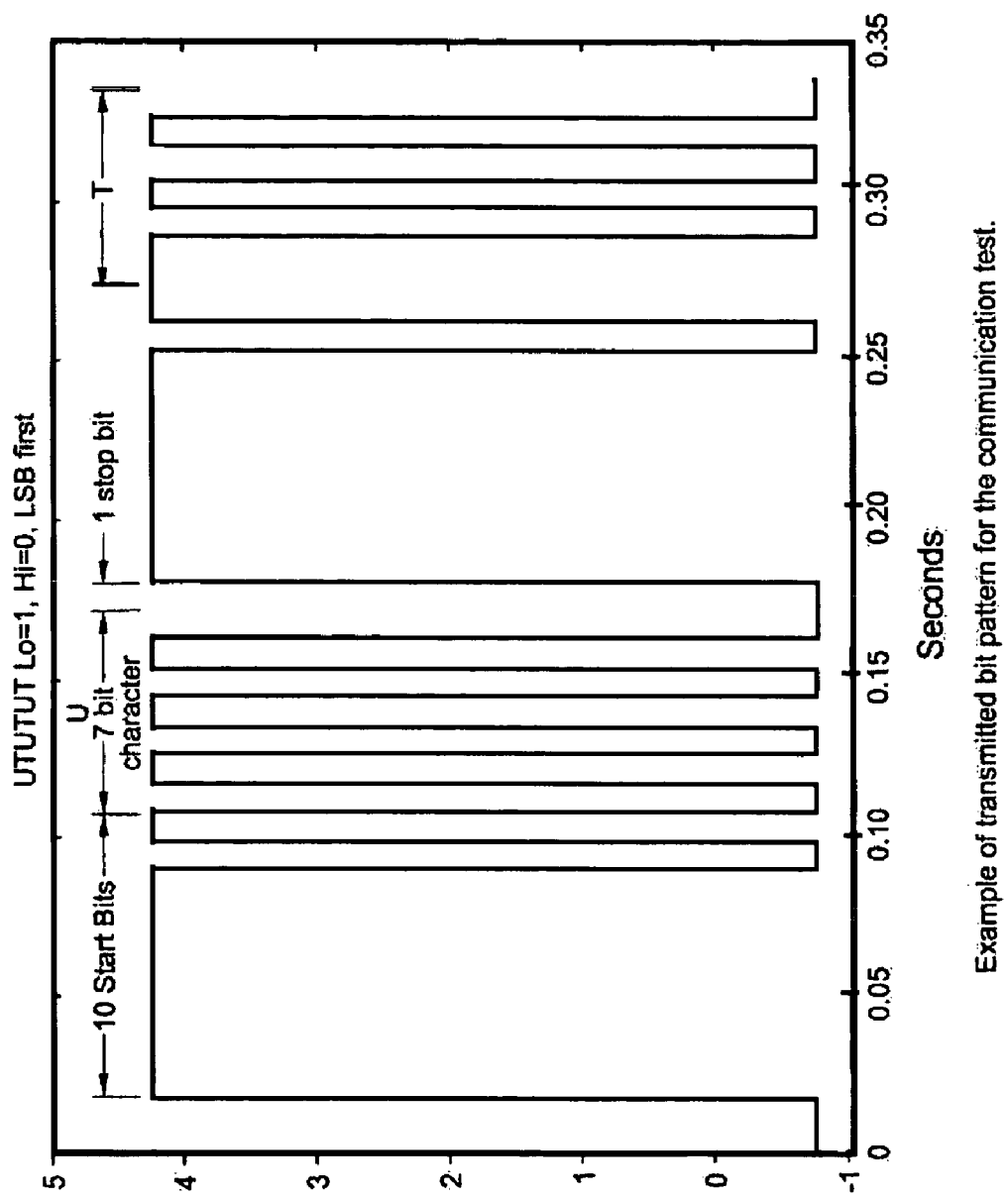
FIG. 19 is a graph illustrating transmitted bit pattern for communication according to an embodiment of a system of the present invention.

For a second set of tests, an arbitrary bit pattern was transmitted. A computer running HyperTerminal was used to send text files through a serial port (RS232), where the serial port signal was used in place of the pulse generator to trigger either f1 or f2 (see FIG. 16). The HyperTerminal encodes each character in the text file into ASCII code and sends it out of the serial port together with the start and stop bits. The minimum bit rate the PC can output, however, is 110 bps, which was at the limit of the transmission speed because of ISI. The other consideration in using a serial port is that it outputs a pulse only during bit transitions (0 to 1 or 1 to 0 transition). The serial port output was used to trigger two function generators, which burst 100 cycles at either f1 or f2. The outputs of the two function generators were added and sent to the transmitter. Again, the signal amplitude from the function generator was kept below 2 Vpp to prevent harmonics generated by the transducer (used 1 Vpp and amplified+40 dB the received signal). The settings for the HyperTerminal are bit rate=110, parity=none, data bits=7, stop bits=1, flow control=Xon/Xoff. For these settings, the output will consist of 18 bits per character; 10 start bits, 7 bits for the ASCII, and 1 stop bit. In addition, it sends the LSB of the ASCII code first. FIG. 19 illustrates a bit pattern sent where the characters "U" (1010101) and "T" (1010100) was sent. Moreover, ones and zeros are mapped to low and high respectively, and start bits=0000000010 and stop bit=1.

The digital oscilloscope 76' used in this example to capture the receive waveform was a NI DAQ card (6062E and SCB-68) and software. Bits were successfully transmitted across an aluminum plate, lap joints and a composite plate. The correlation ($I_2+Q_2$) is plotted in FIGS. 20A-20B for a 1010101011000-bit pattern with a bit rate 110 bps across an aluminum plate. From the plot in FIGS. 20A-20B, it is recommended that the bit rate should be reduced to about 80 bps. Successful communication (at 110 bps), however, was still achieved, in this example, but there were some errors due to multipath interference and/or nulls. Although nulls are less likely to happen (on the aluminum plate) for the entire bit period due to multipath, signal amplitude can significantly decrease in segments at the start of the bit period. This can cause correlations to drop and can lead to errors.

Figure 21:
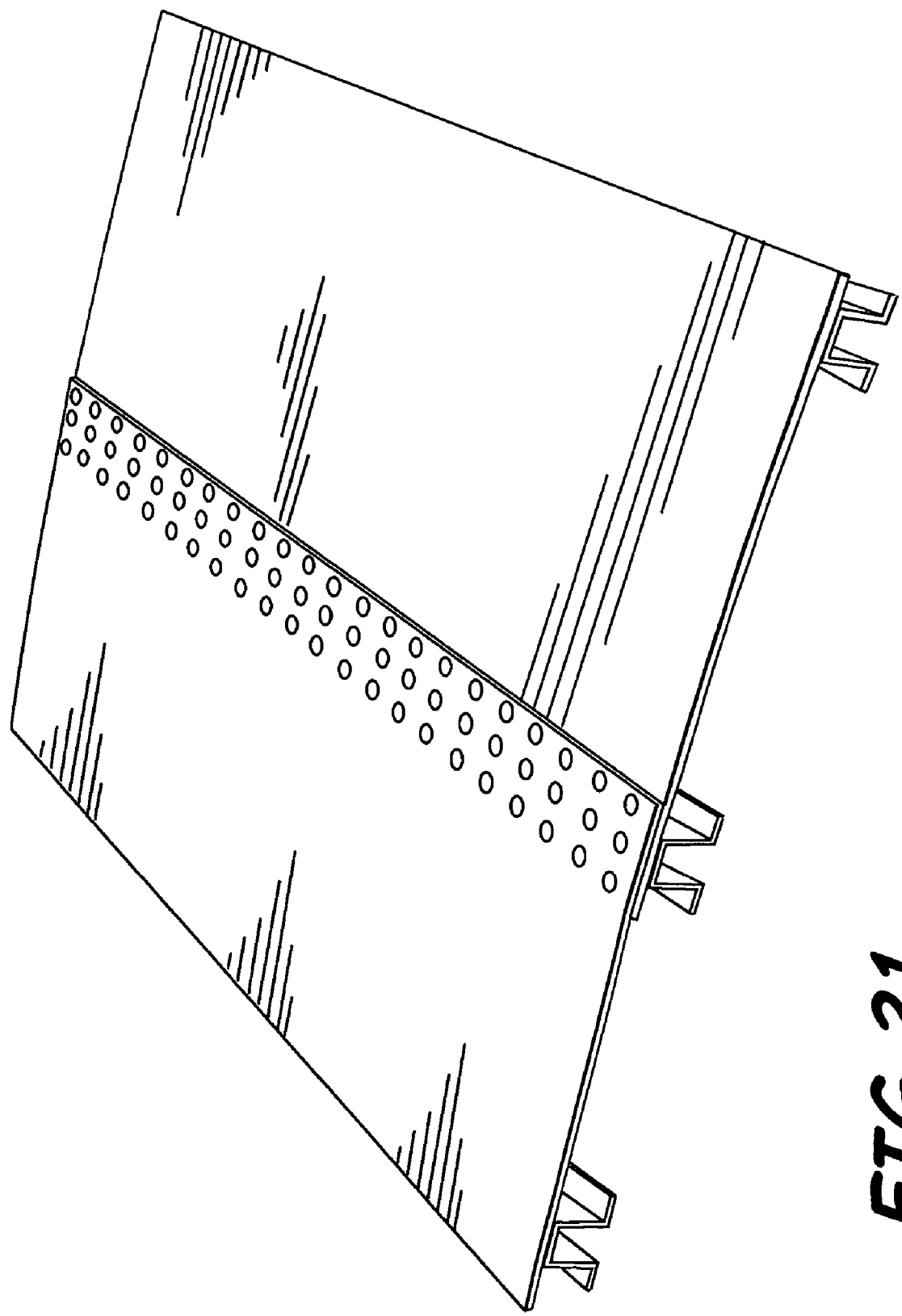
FIG. 21 is a perspective view of a lap joint of a metal structure according to an embodiment of a system of the present invention.

A section of an aircraft wing containing a riveted lap joint were used to measure ultrasound signal attenuation across the joint (see FIG. 21). Measurements in the lab indicate the signals through lap joints are largely attenuated or absorbed. At a distance of 6 inches, the decrease in signal amplitude is about 90% across one lap joint. The signal absorption across lap joints also helps decrease multipath interference, which decreases ISI and allows a higher bit rate. The plot of the signal and the signal's spectrogram is plotted in FIGS. 22A-22B for a 101010-bit pattern. With this signal, bit rates can be increased to about 400 bps. Note that nulls across lap joints are more likely to happen compared to aluminum plates.

Figure 23:
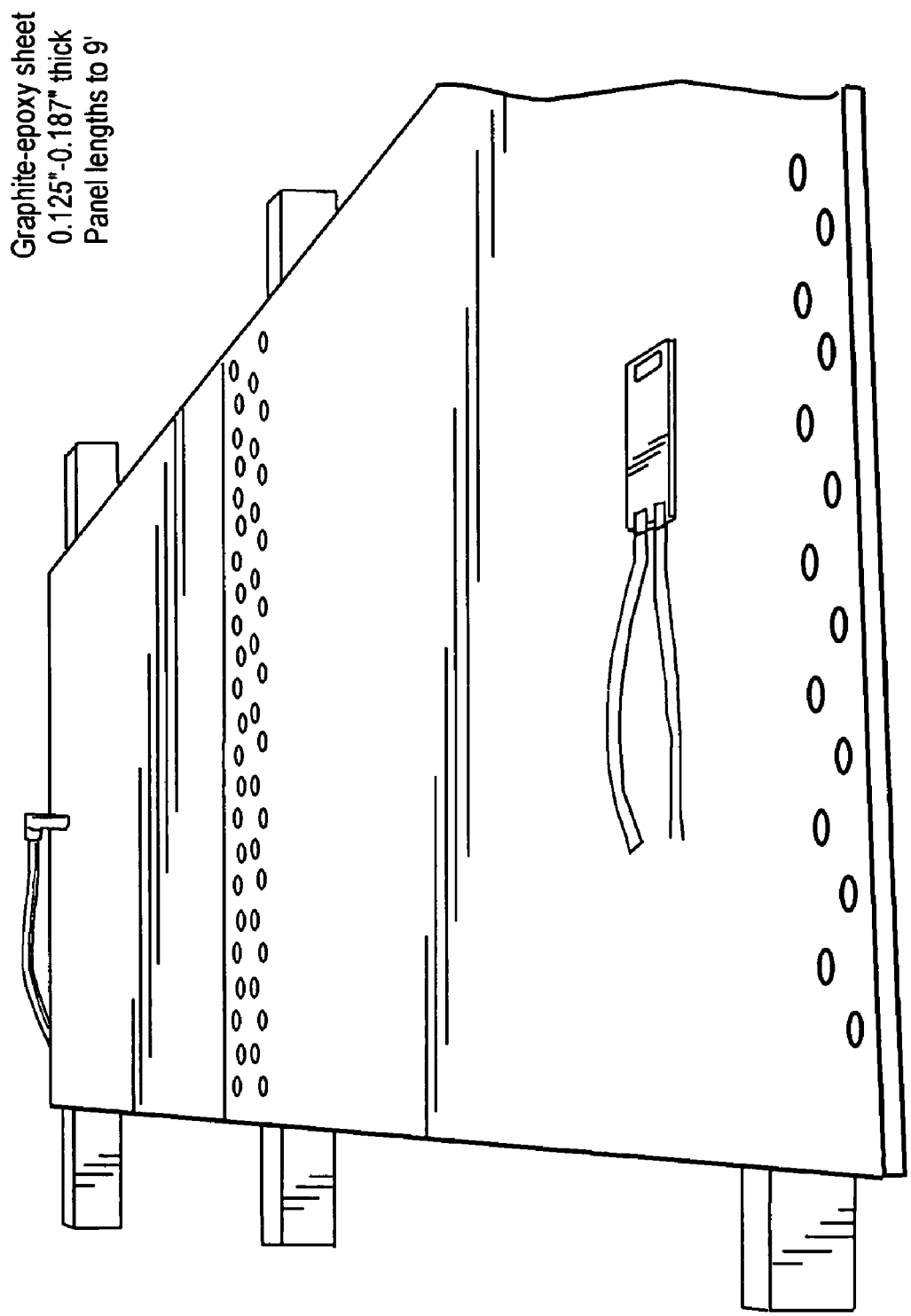
FIG. 23 is a perspective view of a composite plate of a structure according to an embodiment of a system of the present invention.
Figure 24A:
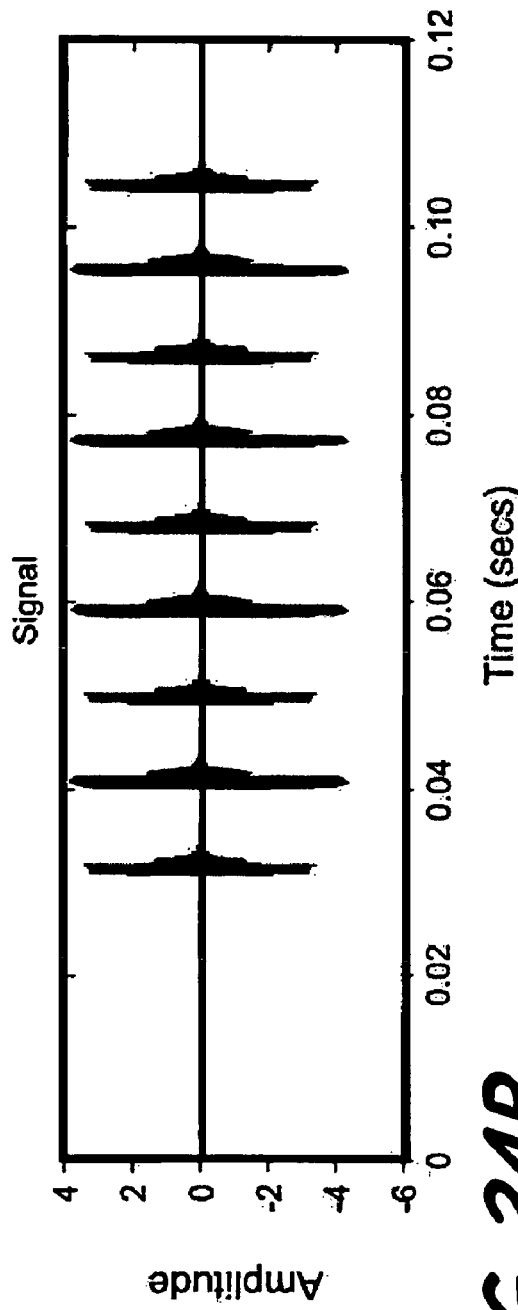
FIG. 24A-24B are graphs of signal and spectrogram according to an embodiment of a system of the present invention.
Figure 24B:
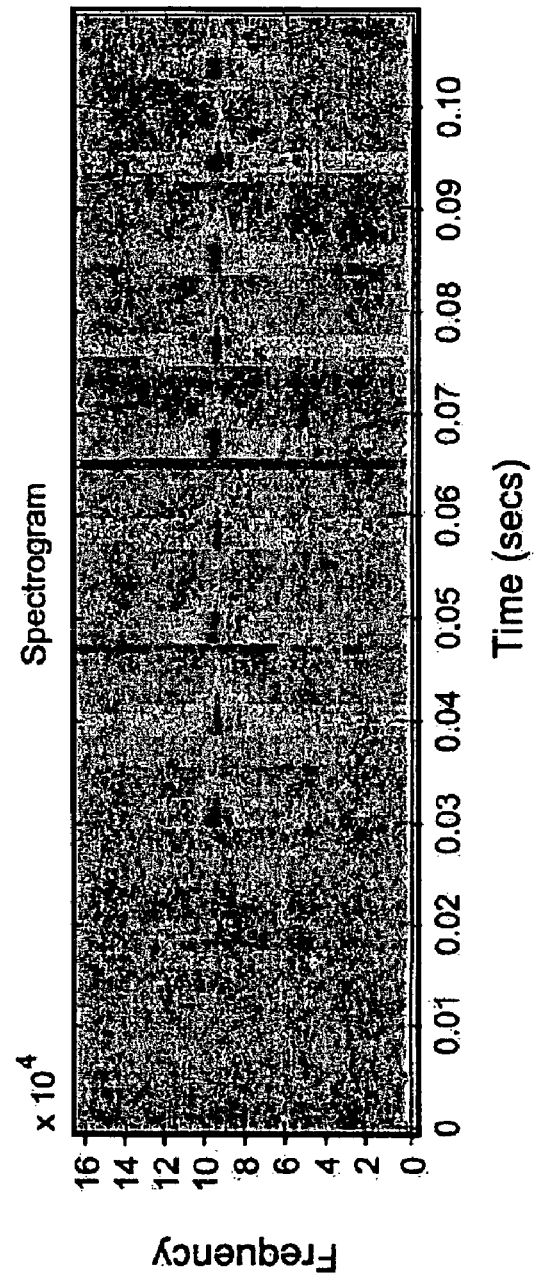

Similarly, measurements were made in the lab on a composite plate (see FIG. 23). Signals traveling across a composite plate are greatly attenuated due to the structure of the material. This will also help reduce multipath interference. Bit rate can be increased to about 300 Hz. A plot of the received signal in a composite plate is shown in FIGS. 24A-24B.

For a digital signal that has two frequency components separated by 2 kHz, sampled above Nyquist and using a rectangular window, a 1 msec segment of the signal is needed to resolve the two frequencies. For frequencies around 100 kHz, this is approximately 100 cycles (200 cycles for frequencies around 200 kHz). Note that the sinusoidal component of the template used for demodulation is 1 msec long.

Figure 25:
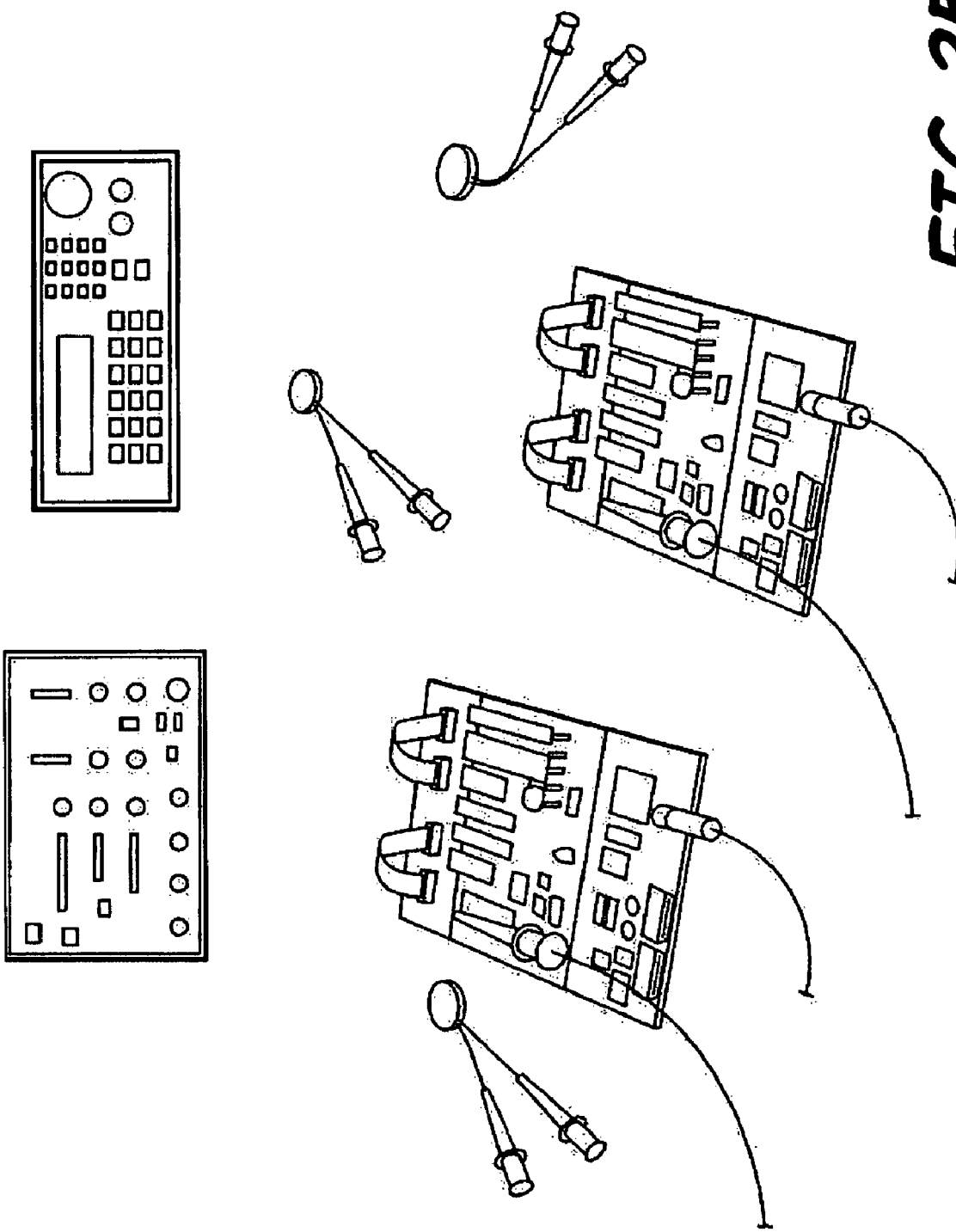
FIG. 25 is a perspective view of a system having dual transmitting according to an embodiment of a system of the present invention.

To perform experiments with multiple transmitters, a simple transmitter was designed using an Atmel AVR board with an Atmega 16 microcontroller running at 16 MHz (see FIG. 25). This eliminated the need for the multiple waveform generators used in the lab tests. Ultrasonic transducers that resonated around 95 kHz were chosen in this example so that symbol separations of one to two kHz could be achieved. With this arrangement frequency tones could be generated in increments defined by:

$$F = \frac{F_o}{N+1}$$

Where $F_o$=8 MHz. Tones of 95 kHz, 93 kHz, 91 kHz, and 89 kHz were used (N=83, 85, 87, 89). The transducers were driven directly from the digital output of the microprocessor with some additional impedance so as not to overdrive the transducers. Symbol separation of approximately 2 kHz was chosen, and channel separation of 2 kHz was also chosen.

An initial test was performed using just one transmitter; in this configuration it was found that long symbol transmission times (approximately 50 cycles per symbol) were needed to produce a point in the signal where the phase of the received signal was stable enough for coherent detection and discrimination to occur. Changing the receiver design to calculate coherence over multiple single cycles rather than multiple cycles may improve the detection. Once reliable single channel operation was established the second transmitter was introduced.

Figure 26:
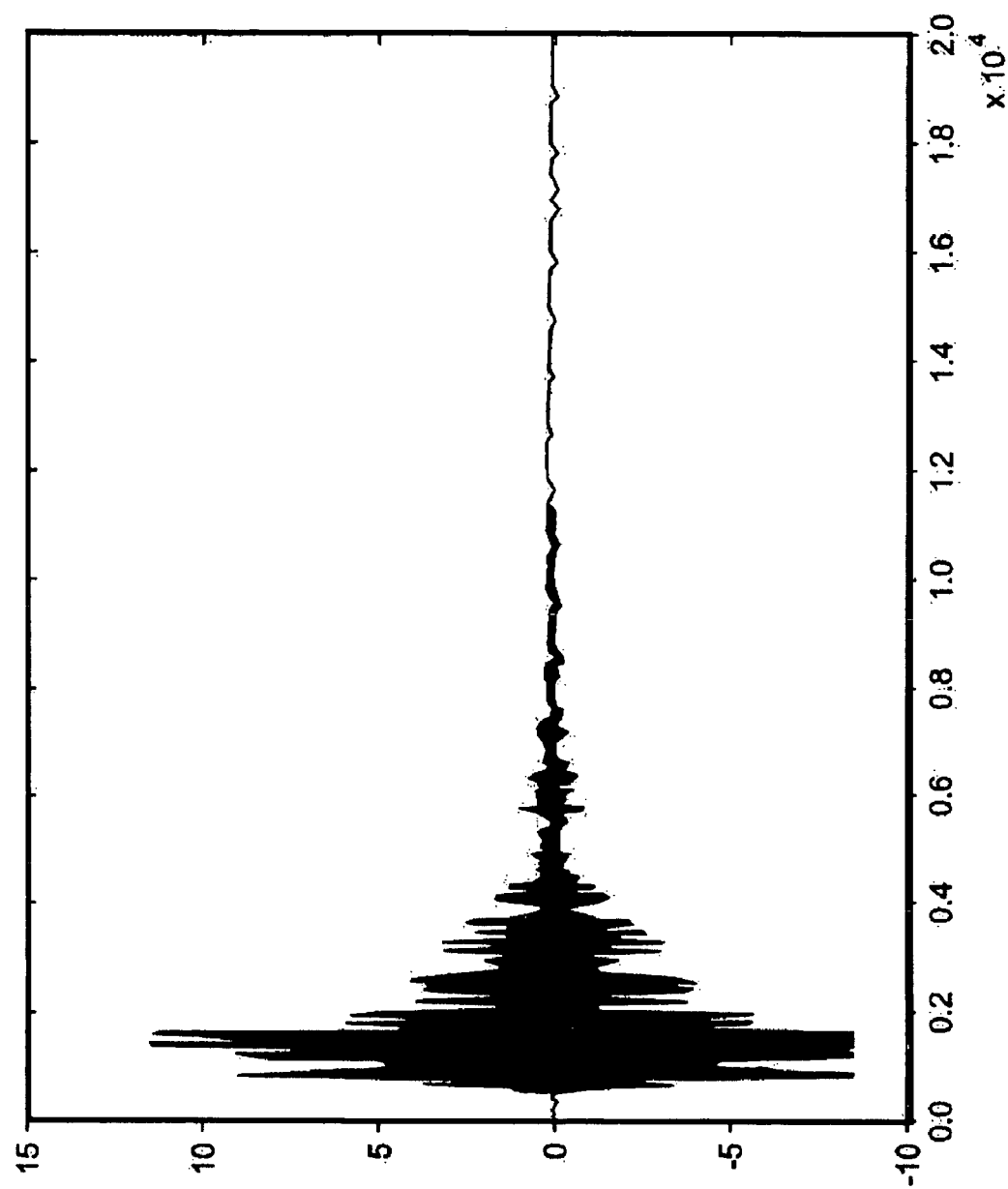
FIG. 26 is a graph of received waveform from two simultaneous transmitters of a system according to an embodiment of the present invention.

For this example, each transmitter transmitted a fixed pseudorandom bit pattern, and they were synchronized so that the transmission occurred at the same time (to maximize the interference from each other). Because multiple transmitters could be set up to reduce collisions, this represents a worst-case situation since. FIG. 26 illustrates the combine waveform from when both transmitters are operating simultaneously, and the symbols are colliding in time.

Figure 27:
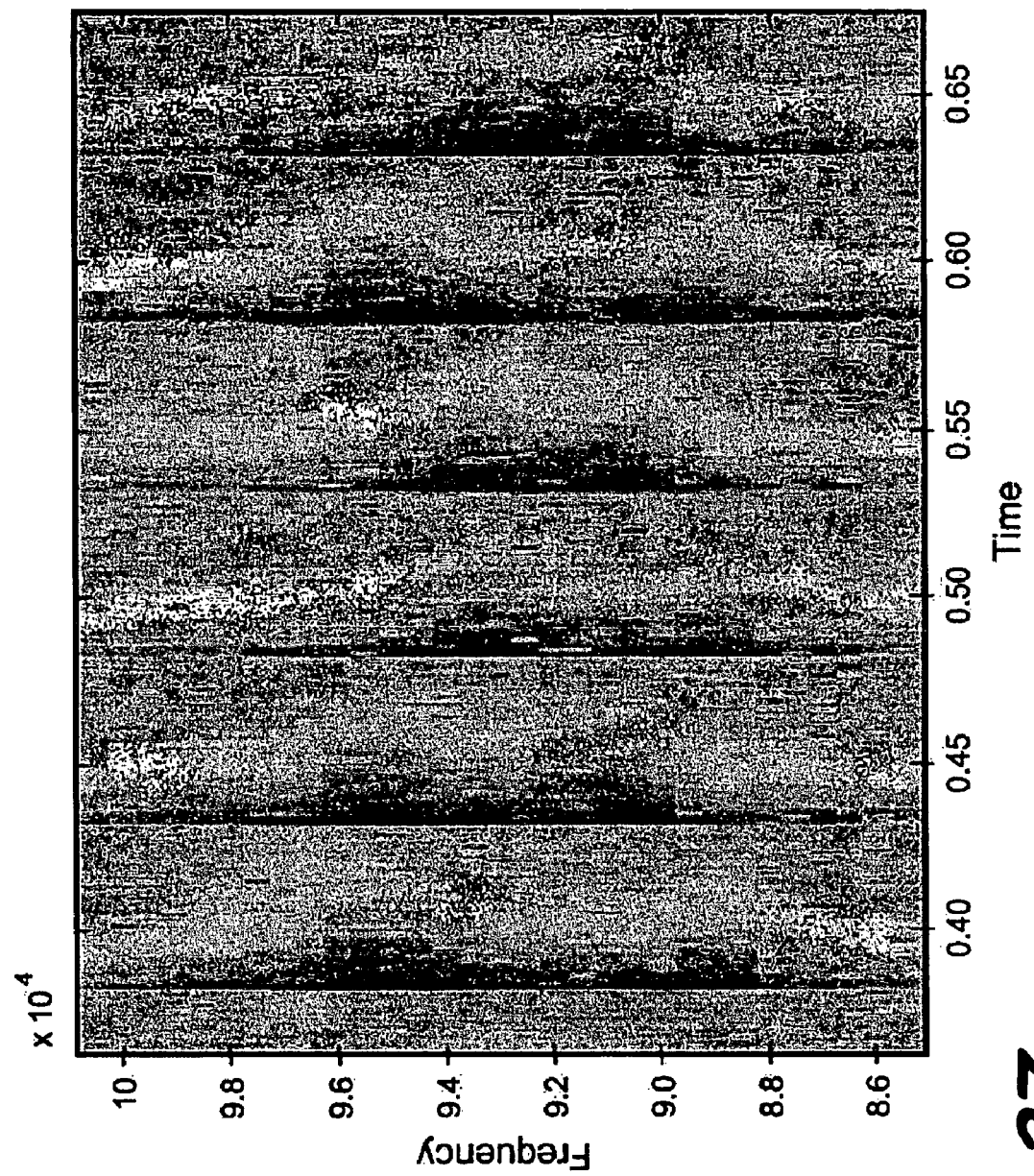
FIG. 27 is a graph of a spectrum of received waveform from multiple bit transmission of a system according to an embodiment of the present invention.

The waveforms were then captured and processed in Matlab with a simple coherent detection method as described earlier herein. The spectrum of the dual transmission is shown in FIG. 27. Although it is difficult to see the four distinct frequency peaks, the coherent detector was able to discriminate each symbol and correctly determine its value. As understood by those skilled in the art, further tests, design refinements and analysis can be made to determine how robust the detection of multiple transmitters will be. This initial example, however, shows that it is indeed possible to communicate on the same plate with multiple ultrasound transmitters.

Based on the communication scheme implemented on the aluminum plate in the example, the power needed for the piezoelectric disk to transmit a message at some message rate can be estimated.

Assumptions:
1) 200 kHz disk, with impedance of 1 k ohm at 78 degrees (this was measured at resonance of the disk).
2) 10-volt driving voltage at the transducer. If run continuously, the transducer would take (10*10/1000)*cos(78 deg)=20 mW.
3) Communication: assume 100 cycles of RF per bit, 50 bits/message, 1 message/min 100*50/200000=25 msec/message 0.025/60=4.2 e-4 duty cycle Average power=4.2 e-4*20 mW=8 uW. This average power is about equal to the power needed to run a low-power clock (32 kHz). The power consumption at a sensor node would be approximately 20 uW, assuming 8 uW for the ultrasound transmitter, 8 uW for the clock, and 4 uW for the processor (operating at 10 duty cycle). For reference, a 20 uW device can run for 1.2 years on a Lithium ion rechargeable coin cell that is 3.2 mm thick (see table from http://www.powerstream.com at FIG. 28).

In other examples, ultrasound propagation measurements were made on the wings of two military aircraft. The objective was to measure the ultrasound signal attenuation of Lamb waves in a wing structure in order to estimate the SNR of a received ultrasound signal for sensor communication. Tests were conducted on an A-10 Thunderbolt ("Warthog") and an F-84 Thunderstreak at the Empire State Aerosciences Museum (Glenville, N.Y.).

Figures 28, 29:
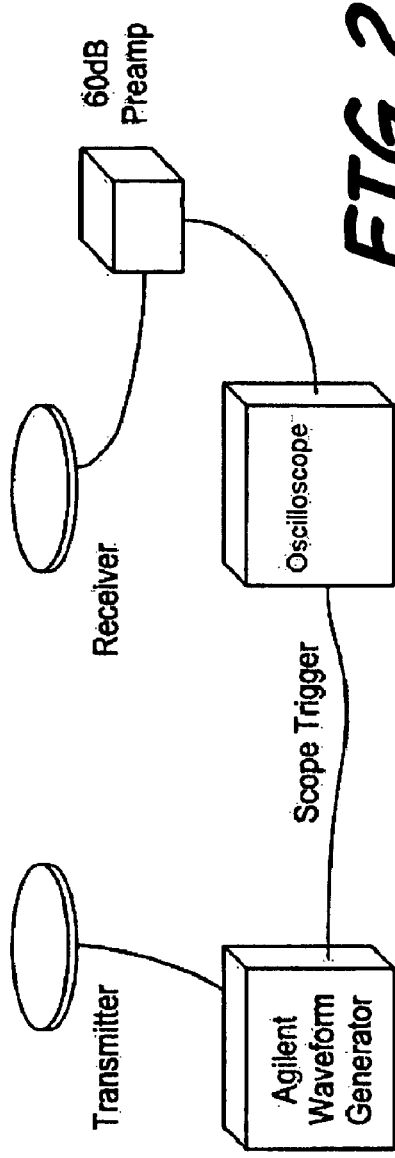
FIG. 28 is a table of electrical characteristics of lithium ion coin cells according to an embodiment of a system of the present invention.
FIG. 29 is a schematic diagram of a system to measure communication according to an embodiment of the present invention.

An embodiment of a system according to the present invention consisted of an Agilent arbitrary waveform generator, two 100 kHz piezoelectric ceramic disks, a signal preamplifier, and an oscilloscope (see FIG. 29). The waveform generator was set up to produce 10 cycles of a square wave at 88 kHz, which was the frequency that gave the maximum signal between the two piezoelectric disks. The peak-to-peak voltage produced by the waveform generator was 5 volts and directly fed the transmitter piezoelectric disk through coax cable. A Panametrics preamplifier with 60 dB of gain was used to amplify signals from the receiver piezoelectric disk. The output of the preamplifier was viewed on the oscilloscope and used to measure peak-to-peak received voltage. The transmitted waveform was also viewed on the oscilloscope to make propagation time measurements between the transmitted and received signal.

The piezoelectric transducers were attached to the wing structure using shearwave couplant and duct tape. The maximum peak-to-peak voltage of the received waveform was recorded, along with the time delay between the start of the transmitted and received waveforms. An estimate was also made of the delay spread, which was the difference in time between the first arriving signal and the last arriving signal from multipath reflections.

Figure 30:
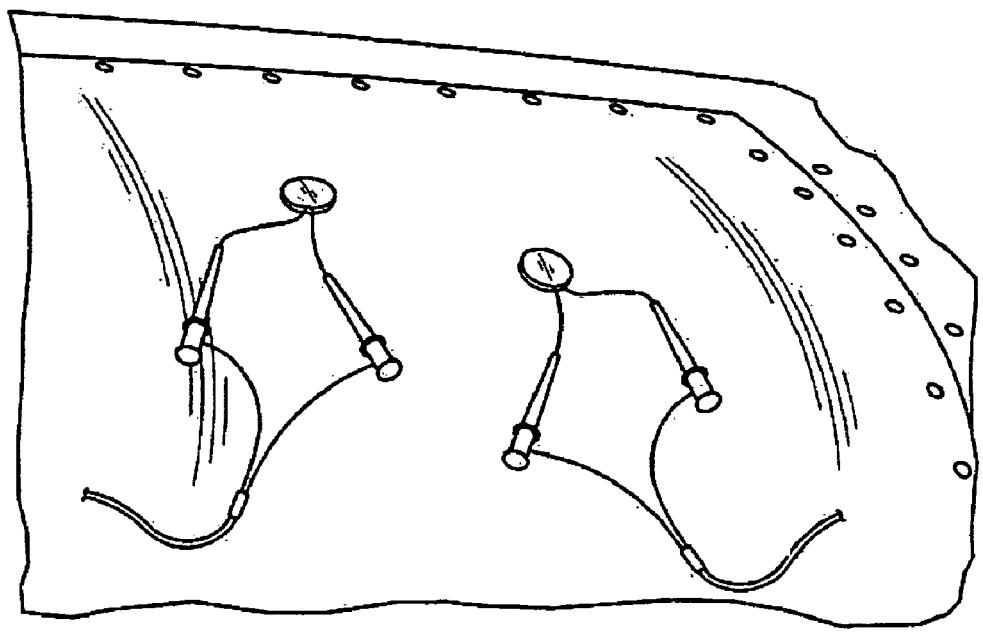
FIG. 30 is a perspective view of transducers mounted on a wing of an aircraft according to an embodiment of a system of the present invention

The first test was performed in an example on the leading edge of an A-10 Thunderbolt wing (see FIG. 30). A 500 mV peak-to-peak (P-P) signal was measured from the receiver with a transmitter/receiver separation of 5 inches, but it may be difficult to get a measurable signal for distances much larger than 5 inches. This is thought to be from poor acoustic coupling through the paint on a wing, or energy leaking from the wing covering to the internal wing supports. Further tests were performed on an F-84 wing, which was not painted.

Figure 31:
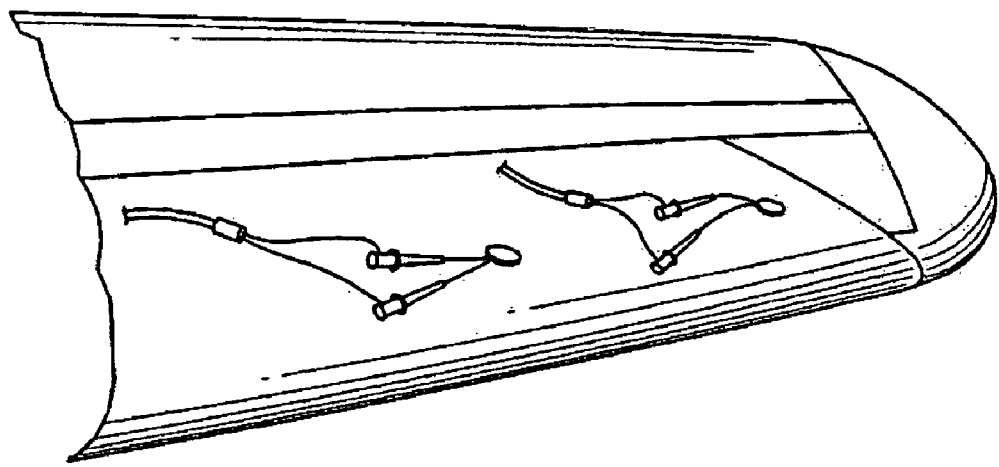
FIG. 31 is a perspective view of transducers mounted on a wing of an aircraft according to an embodiment of a system of the present invention.

Acoustic propagation measurements were made on an F-84 wing at various separations between the transmitter and receiver (see FIG. 31). The aluminum F-84 wing was not painted, and a much stronger received signal was obtained as compared to the A-10 wing. Measurements were also made across riveted lap joints in the wing, and from the wing to the fuselage (see FIG. 33). A summary of the measurements is shown in the table of FIG. 32.

Figures 32, 33:
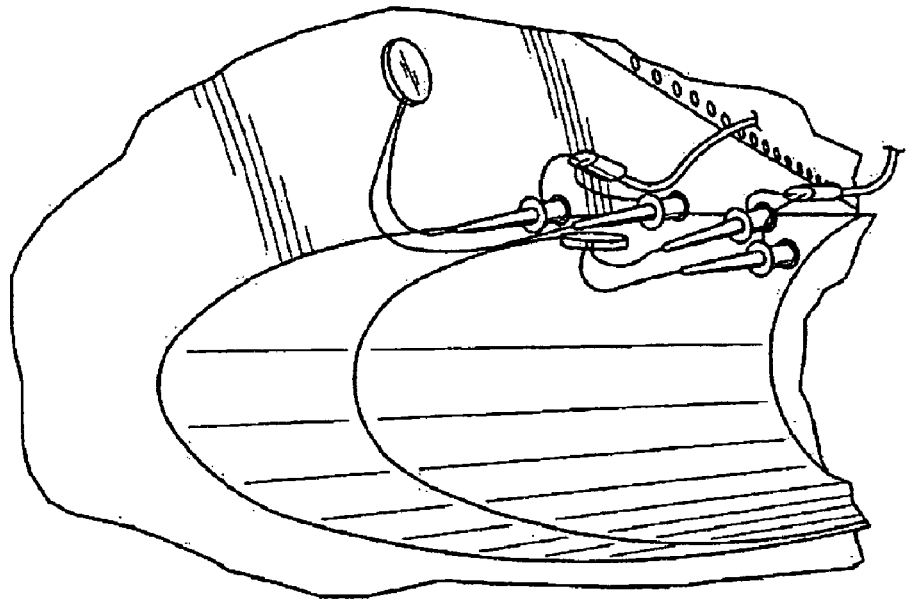
FIG. 32 is a table of acoustic measurements on the structure of FIG. 31 according to an embodiment of a system of the present invention.
FIG. 33 is a perspective view of a system measuring acoustics from a wing to a fuselage of an aircraft according to an embodiment of the present invention.
Figure 34:
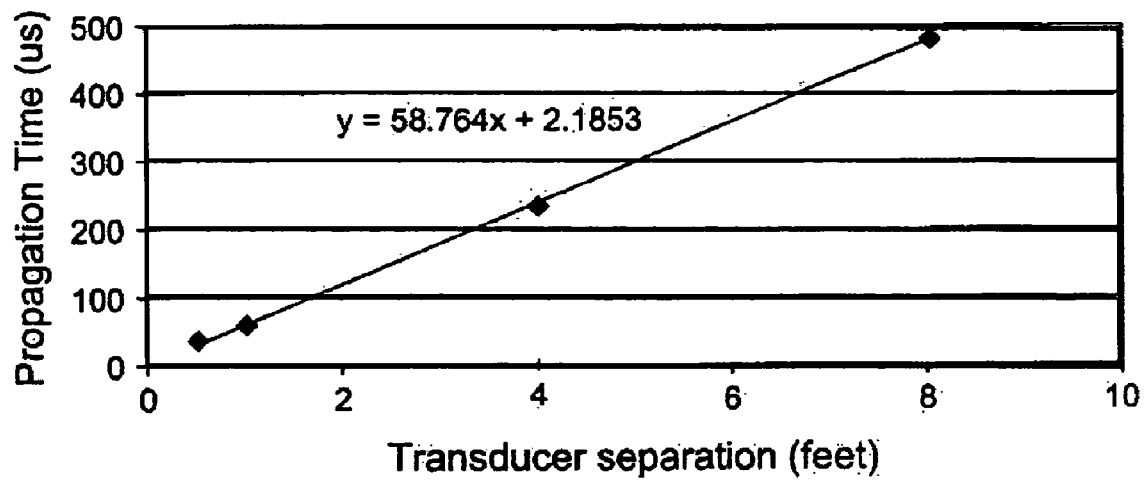
FIG. 34 is a graph of propagation time for non-lap joint measurements according to an embodiment of a system of the present invention.
Figure 35:
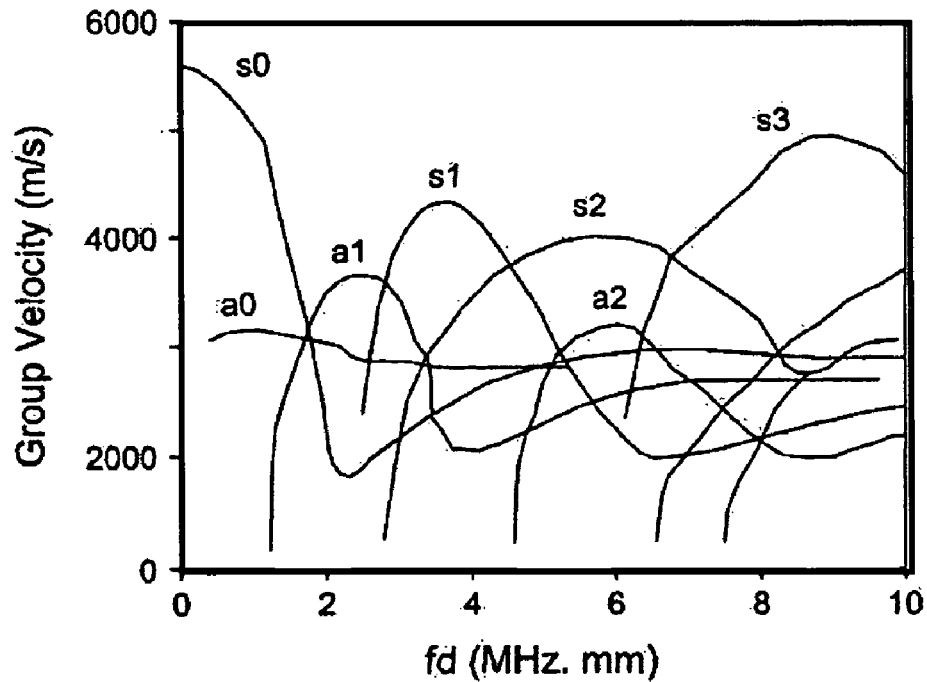
FIG. 35 is a graph of Lamb group velocity dispersion curves for an aluminum plate according to an embodiment of a system of the present invention.

FIG. 32 illustrates a plot of the propagation time of the waveform sent from the transmitter to the receiver for measurement points that did not have a lap joint directly between the transmitter and receiver. The propagation time increases linearly with transducer separation, and the speed of sound measured in the wing was about 5200 m/s. This is consistent with the Lamb wave propagation velocity in an aluminum plate in the s0 mode (see FIG. 35). A 5200 m/s velocity would correspond to an $f_d$ of approximately 0.7, or an aluminum thickness of about 8 mm.

Measurements taken with lap joints in between the transmitter and receiver produced propagation times significantly larger than without lap joints. Propagation times were as much as five times greater than expected from the speed of sound in aluminum. Because there are no Lamb wave propagation modes that could have resulted in these propagation times, the signals are from multipath reflections. For the measurement point at 10-foot separation, the propagation time corresponds to a signal that traveled over 30 feet. The delay spread values for the measurements also confirm that multipath propagation exists for all the measurement points and that the multipath energy can travel a great distance before being received (15-30 feet).

Figure 36:
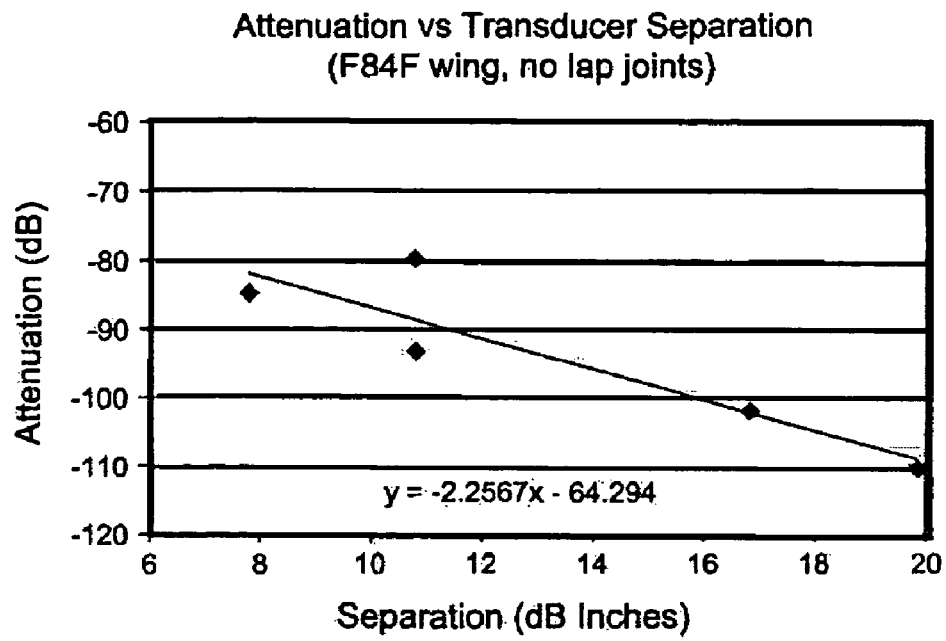
FIG. 36 is a graph of signal attenuation versus transducer separation for a wing of an aircraft according to an embodiment of a system of the present invention.
Figure 37:
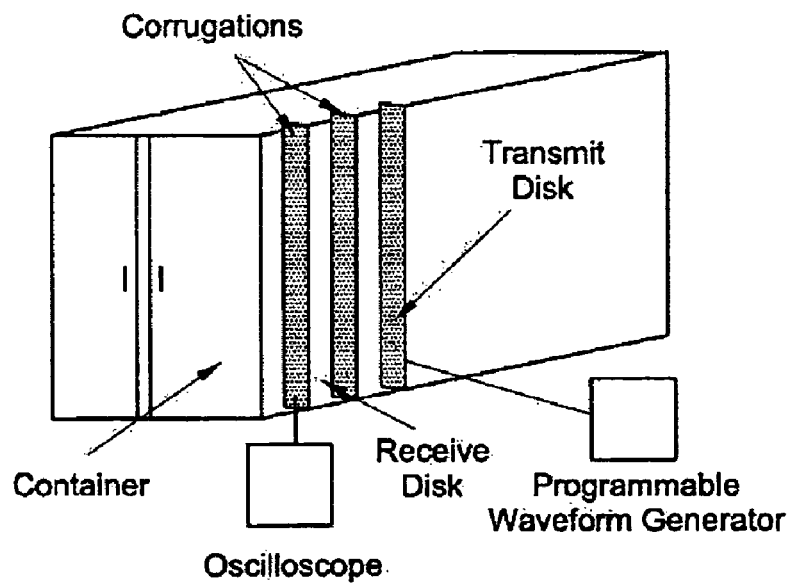
FIG. 37 is a schematic diagram of a system to measure a shipping container according to an embodiment of the present invention.

FIG. 36 illustrates a plot of the signal attenuation from the transmitter to the receiver for the non-lap joint measurements on the F-84 wing. The attenuation includes all measurement system losses from signal transmission and reception as well as the signal attenuation in the wing itself. The amplifier was assumed to provide 60 dB of gain, although this was not measured. The received signal measurements at the same transducer separation tend to be variable because of differences in transducer coupling to the wing. It, however, can be estimated from the slope of the attenuation data signal attenuation from the wing to be approximately 2.5-4 dB/ft. This is significantly greater than the 1.6 dB/ft attenuation that was measured on a steel shipping container (see other example described further herein), and is probably due to acoustic losses at the wing-skin/wing-rib joints. The slope of the best-fit line to the data, plotted on a log-log scale, is −2.26. Because the spreading loss in the plate ($L_s$) is 1/R, the attenuation from absorption and scattering ($L_m$) is approximately $1/R^{1.26}$. It can also be noted that a 60 dB signal preamplifier was needed to obtain adequate signal levels for the wing measurements, while this preamplifier was not needed for measurements on a free plate or the steel shipping container. The source of the extra signal loss in the F-84 wing measurements is not known.

Ultrasound propagation measurements have been made on the aluminum wing of two aircraft. It can be feasible to obtain enough signal strength to communicate signals the length of the wing using modulated ultrasound if no paint is present on the wing, and the energy from multipath reflections can be utilized. Multipath reflections may be important to allow sound propagation around lap joints and other structure in the wing that may significantly attenuate the signal.

To illustrate using ultrasound for sensor communication within a shipping container, an example of ultrasound attenuation measurements were made on a 40-foot ISO shipping container. The measurements were performed to see if an ultrasound signal could be used for communication between a sensor mounted on one end of the container, and a processor mounted at the other end of the container. Initial results indicate that for an 85 kHz signal, the ultrasound attenuation is about 1 dB per foot, which should be low enough to support communication down the container.

In this example of an embodiment of a system of the present invention, two piezoelectric ceramic disks (1" diameter, 0.1" thick) from APC International (p/n D-1.000-0.100-850) were attached to the side of a 40' ISO steel shipping container using ultrasonic shear wave couplant (Sonotech Shear Gel). The receiving disk was placed on the outcropping of the last corrugation on the container side, and the transmitting disk was placed at different corrugations along the side (see FIG. 37). An Agilent programmable waveform generator was used to drive the transmitter, and the peak-to-peak voltage of the received waveform was viewed on an oscilloscope. The transmitter frequency was adjusted to 85 kHz to produce a maximum received waveform voltage. The transmit voltage was 5 cycles of a 10 volt square wave.

A table of received voltage for different transmitter locations is shown in FIG. 38. FIG. 39 is a plot of the attenuation as a function distance on a log-log scale for the points that include steel corrugations between the transmitter and receiver (all but the first point). From these measurements, one can conclude that the acoustic coupling efficiency into and out of the container is fairly poor (−38.4 dB), but the attenuation introduced from propagation down the side of the container is fairly low (14 dB per 9 corrugations). The slope of the attenuation line indicates that the loss factor due to sound absorption and scattering (Lm) is about ($1/R_{0.6}$), which is considerably lower that the $1/R_{1.26}$ loss factor measured for the aircraft wing. Total attenuation from propagation along the container side would be about 14×4=46 dB, which is relatively low. This means that acoustic communication from end-to-end on a container is feasible.

Based on the results of the lab and field measurements, a measurement of the noise in the ultrasound frequency range (50 kHz-300 kHz) generated by an operating engine can be performed. Because it is feasible to communicate over 50 feet on an aircraft wing using ultrasound with no engine noise, knowing the noise level introduced by a running engine can allow the design of the best modulation and receiver approach to meet the communication requirements. Noise measurements can be performed at a test facility for a structure such as at the GE Aircraft Engine test facility in Peebles, Ohio. The Peebles facility has cabling from the engine test stand to a control building. This cabling can be used to monitor signals from ultrasound transducers mounted on the engine test stand to determine how much noise is coupled from the engine under different engine speeds.

Figure 40:
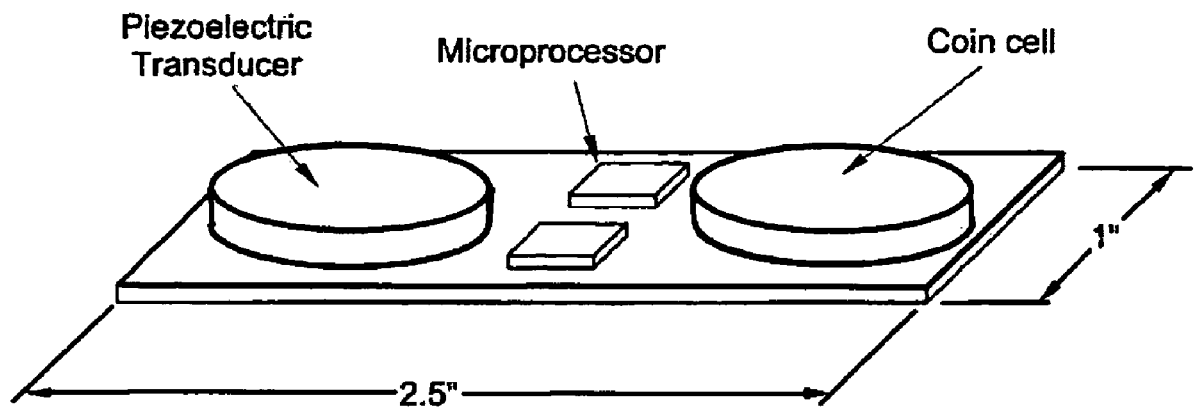
FIG. 40 is a perspective view of a package for a sensor node with ultrasound communication according to a table illustrating attenuation measurements for a shipping container structure according to an embodiment of the present invention.

It also is possible to make a low-power, battery powered ultrasound communication device based on the hardware used in the multiple transmitter example. The Atmel processor contains A/D input ports that can be used to read sensors, and the digital output can be used to drive the transmit ultrasound transducer. One or two Lithium coin cells can provide power for the unit. The devices can be housed in a 2.5 inches×1 inch×0.16 inch package such as shown in FIG. 40, including transducer, batteries, and electronics.

Ultrasound communication is a viable approach to low bit rate sensor communication in aircraft wing and other structures. Communication has been demonstrated in an aluminum plate for a single transmitter/receiver, and multiple transmitters operating simultaneously. Theoretical link budget and experimental attenuation measurements confirm that there is adequate SNR for communication in aluminum aircraft wing skin and shipping container structures.

In the drawings and specification, there have been disclosed embodiments of the invention and, although specific terms are employed, they are used in a generic and descriptive sense only and not for the purpose of limitation, the scope of the invention being set forth in the following claims.

That claimed is:

1. An ultrasound communication system embedded in a metal airframe structure, of an aircraft, the system comprising:
    an aircraft having a metal airframe structure;
    a plurality of wireless ultrasound transmitters embedded in the metal airframe structure, to operate asynchronously and transmit modulated ultrasound communications along the metal airframe structure;
    a modulator in communication with each of the plurality of wireless ultrasound transmitters to modulate each of the plurality of wireless ultrasound transmitters so that Lamb waves are propagated along the metal airframe structure; and
    an ultrasound receiver positioned remote from the plurality of wireless ultrasound transmitters and connected to the aircraft to receive modulated ultrasound communication from the plurality of wireless ultrasound transmitters.

2. A system as defined in claim 1, wherein the modulator includes a frequency generator to initiate a frequency hopping scheme among the plurality of wireless ultrasound transmitters to thereby digitally encode transducer information among the different ones of the plurality of wireless ultrasound transmitters.

3. A system as defined in claim 2, wherein the modulator includes a frequency-lap generator to generate digitally encoded frequency lapping among different ones of the plurality of ultrasound transmitters, wherein the ultrasound receiver is selected from the group of: a relatively larger receiver or a phased array receiver, and wherein the ultrasound receiver has a frequency range between about 50 kHz and about 300 kHz.

4. A system as defined in claim 1, wherein the airframe structure is selected from the group of: a wing of an aircraft, a fuselage of an aircraft, a metal plate of an aircraft, or skin of an aircraft wing, and wherein the ultrasound receiver includes a channel equalizer to reduce the effects of signal multipath and a decoder to decode the modulated ultrasound communication.

5. A system as defined in claim 1, wherein the airframe structure includes at least one lap joint positioned between at least one of the plurality of ultrasound transmitters and the ultrasound receiver, wherein the ultrasound communication within the system is only one-way between each of the plurality of ultrasound transmitters and the ultrasound receiver, and wherein each of the plurality of ultrasound transmitters and the ultrasound receiver includes a piezoelectric device.

6. A system as defined in claim 1, wherein the plurality of ultrasound transmitters and the ultrasound receiver are positioned spaced-apart so that each of the plurality of ultrasound transmitters is positioned within a predetermined distance from the ultrasound receiver, the predetermined distance being selected responsive to a predetermined communication link budget.

7. An ultrasound communication system to embed in metal structure, the system comprising:
  a metal structure;
  a plurality of wireless ultrasound transmitters each connected to and spaced-apart along the metal structure to transmit modulated ultrasound communications along the structure;
  an ultrasound receiver positioned remote from the plurality of ultrasound transmitters and connected to the structure to receive modulated ultrasound communication from each of the plurality of ultrasound transmitters; and
  at least one modulator in communication with each of the plurality of ultrasound transmitters to modulate each of the plurality of ultrasound transducers so that modulated ultrasound communications is transmitted from each of the plurality of ultrasound transmitters, the plurality of ultrasound transmitters being operable asynchronously to transmit ultrasound communication to the ultrasound receiver, and the ultrasound receiver including a channel equalizer to reduce the effects of signal multipath and a decoder to decode the modulated ultrasound communication received from each of the plurality of ultrasound transmitters.

8. A system as defined in claim 7, wherein the modulator includes a frequency-lap generator to generate digitally encoded frequency lapping among different ones of the plurality of ultrasound transmitters, and wherein the structure selected from the group of a metal material or a composite material.

9. An ultrasound communication system to embed in metal structure, the system comprising:
  a metal structure, the metal structure being selected from the group of: an airframe, a wing of an aircraft, a fuselage of an aircraft, a shipping container, a pipe, a bridge frame, a metal plate, or skin of an aircraft wing;
  a plurality of wireless ultrasound transmitters each connected to and spaced-apart along the metal structure to transmit modulated ultrasound communications along the structure, each of the plurality of ultrasound transmitters and the ultrasound receiver including a piezoelectric device; and
  an ultrasound receiver positioned remote from the plurality of ultrasound transmitters and connected to the structure to receive modulated ultrasound communication from each of the plurality of ultrasound transmitters, the structure also including at least one lap joint positioned between at least one of the plurality of ultrasound transmitters and the ultrasound receiver, the ultrasound communication within the system being only one-way between each of the plurality of ultrasound transmitters and the ultrasound receiver.

10. A system as defined in claim 9, wherein the ultrasound receiver is selected from the group of a relatively larger receiver or a phased array receiver, and wherein the ultrasound receiver has a frequency range between about 50 kHz and about 300 kHz.

11. A system as defined in claim 7, wherein the plurality of ultrasound transmitters and the ultrasound receiver are positioned spaced-apart so that each of the plurality of ultrasound transmitters is positioned within a predetermined distance from the ultrasound receiver, the predetermined distance being selected responsive to a predetermined communication link budget.

12. A method of ultrasound communication, the method comprising:
  mounting a plurality of ultrasound transmitters in spaced-apart relation along a structure;
  mounting an ultrasound receiver to the structure remote from each of the plurality of ultrasound transmitters;
  modulating each of the plurality of transmitters with a preselected modulation scheme; transmitting ultrasound data communication from at least one of the plurality of transmitters along the structure to the ultrasound receiver;
  receiving the ultrasound communication at the ultrasound receiver; and
  demodulating the received ultrasound communication.

13. A method as defined in claim 12, wherein the modulating step includes generating digitally encoded frequency lapping among different ones of the plurality of ultrasound transmitters.

14. A method as defined in claim 12, wherein the step of mounting the plurality of ultrasound transmitters includes mounting at least one of the plurality of ultrasound transmitters so that a lap joint associated with the structure is positioned between the at least one of the plurality of ultrasound transmitters and the ultrasound receiver.

15. A method as defined in claim 12, wherein the respective mountings of each of the plurality of ultrasound transmitters and the ultrasound receiver on the structure are located responsive to a predetermined communication link budget.

16. A method as defined in claim 12, wherein the ultrasound communications includes data indicative of stress of the structure, and the method further comprising determining structure stress responsive to the received ultrasound communications.

17. A method as defined in claim 12, wherein in the step of transmitting includes propagating Lamb waves along the structure to the ultrasound receiver.

18. A method as defined in claim 17, wherein the step of receiving includes receiving multipath ultrasound energy from along the structure and channel equalizing the received ultrasound communication to reduce the effects of the multipath ultrasound energy on the received ultrasound communication.

19. An ultrasound communication system having at least portions thereof embedded in a metal structure, the system comprising:
  a metal structure;
  a plurality of wireless ultrasound transmitters each embedded in the metal structure so that when operating each of the plurality of wireless ultrasound transmitters transmits ultrasound communication along the metal structure;
  a modulator in communication with each of the plurality of wireless ultrasound transmitters to modulate each of the plurality of wireless ultrasound transmitters so that Lamb waves are propagated along the metal structure, the modulator including a frequency generator to generate a frequency scheme among the plurality of wireless transmitters, the frequency generator comprising a frequency-lap generator to thereby digitally encode frequency lapping among different ones of the plurality of wireless ultrasound transmitters; and an ultrasound receiver posited remote from each of the plurality of wireless ultrasound transmitters and connected to the metal structure so that when operating the ultrasound receiver receives modulated and transmitted ultrasound communication propagating as Lamb waves along the metal structure from each of the plurality of wireless ultrasound transmitters, the receiver being positioned at a distance from each of the plurality of wireless ultrasound transmitters based on a predetermined communication link budget, having a channel equalizer to reduce the effects of signal multipath, and having a decoder to decode the modulated ultrasound communication received from each of the plurality of wireless ultrasound transmitters.

20. A system as defined in claim 19, wherein the predetermined communication link budget includes the required transmit power needed to communicate ultrasound communication over a given distance in the metal structure, takes into account multipath reflections, and provides an estimate of the carrier-to-noise ratio.

21. A system as defined in claim 20, wherein the receiver receives the ultrasound communication at a relative lower acoustic frequency in the range between about 50 kHz to about 300 kHz.

22. A system as defined in claim 21, wherein the metal structure comprises a wing of an aircraft, wherein the communication link budget is a function of environmental noise generated from one or more engines of the aircraft, and wherein the wing includes one or more lap joints formed therein.

23. A system as defined in claim 22, wherein the receiver is positioned to receive ultrasound communication substantial across the entire length of the wing of the aircraft, and wherein the receiver utilizes multipath reflections to obtain enough signal strength to receive the modulated and transmitted ultrasound communication.

* * * * *

UNITED STATES PATENT AND TRADEMARK OFFICE
CERTIFICATE OF CORRECTION

PATENT NO.        : 7,654,148 B2
APPLICATION NO.   : 11/417421
DATED             : February 2, 2010
INVENTOR(S)       : Tomlinson, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 596 days.

Signed and Sealed this

Twenty-third Day of November, 2010

David J. Kappos
*Director of the United States Patent and Trademark Office*